US009349159B2

(12) United States Patent
Yaguchi et al.

(10) Patent No.: US 9,349,159 B2
(45) Date of Patent: May 24, 2016

(54) IMAGE PROCESSING DEVICE, IMAGE PROCESSING METHOD, AND INFORMATION STORAGE DEVICE

(71) Applicant: OLYMPUS CORPORATION, Shibuya-ku, Tokyo (JP)

(72) Inventors: Yoichi Yaguchi, Hino (JP); Ronee Asad, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/697,272

(22) Filed: Apr. 27, 2015

(65) Prior Publication Data

US 2015/0228056 A1    Aug. 13, 2015

Related U.S. Application Data

(63) Continuation of application No. PCT/JP2013/084188, filed on Dec. 20, 2013.

(30) Foreign Application Priority Data

Dec. 28, 2012    (JP) .................. 2012-287572

(51) Int. Cl.
*G06T 3/40* (2006.01)
*A61B 1/00* (2006.01)
(Continued)

(52) U.S. Cl.
CPC ........... *G06T 3/4038* (2013.01); *A61B 1/00009* (2013.01); *A61B 1/041* (2013.01);
(Continued)

(58) Field of Classification Search
CPC ....... G06T 5/50; G06T 7/0014; G06T 7/2053; G06T 2207/10016; G06T 2207/10068; G06T 2207/30028; G06T 2207/30096; G06T 3/4038; G06T 7/0012; G06T 2207/30196; G06T 2207/20221; G06T 2207/20224; G06T 7/0024; A61B 1/00009; A61B 1/041; G06K 9/4604; G06K 9/6203; G06K 9/6215; G06K 2209/05; G06K 9/00765; G06K 9/00751; G06K 9/68; H04N 5/76; G06F 17/30843; G06F 19/321; G11B 27/031; G11B 27/105; G11B 27/28
USPC .......... 382/282, 128, 130, 131, 255; 348/239, 348/E05.053
See application file for complete search history.

(56) References Cited

U.S. PATENT DOCUMENTS

2007/0060798 A1    3/2007 Krupnik et al.
2007/0171279 A1    7/2007 Hasegawa et al.
(Continued)

FOREIGN PATENT DOCUMENTS

JP    11220689 A     8/1999
JP    2007195586 A   8/2007
(Continued)

OTHER PUBLICATIONS

International Search Report (ISR) dated Jan. 21, 2014 issued in International Application No. PCT/JP2013/084188.

*Primary Examiner* — Mekonen Bekele
(74) *Attorney, Agent, or Firm* — Holtz, Holtz & Volek PC

(57) ABSTRACT

An image processing device includes an image sequence acquisition section that acquires an input image sequence that includes first to N-th images, and a processing section that performs an image summarization process that deletes some of the first to Nth images to generate a summary image sequence, the processing section selecting an s-th (s is an integer that satisfies 0≤s≤N+1) image to be a provisional summary image, selecting a t-th (t is an integer that satisfies 0≤t≤s−1) image to be a provisional preceding summary image, selecting a u-th (u is an integer that satisfies t<u<s) image to be a determination target image, calculating a summarization interval evaluation value G(t, s) based on deformation information about the provisional summary image and the determination target image, and deformation information about the provisional preceding summary image and the determination target image, and performing the image summarization process.

14 Claims, 19 Drawing Sheets

(51) Int. Cl.
*A61B 1/04* (2006.01)
*G06T 7/00* (2006.01)
*G11B 27/031* (2006.01)
*G06F 17/30* (2006.01)
*G11B 27/10* (2006.01)
*G11B 27/28* (2006.01)

(52) U.S. Cl.
CPC ........ *G06F17/30843* (2013.01); *G06T 7/0012* (2013.01); *G11B 27/031* (2013.01); *G11B 27/105* (2013.01); *G11B 27/28* (2013.01); *G06T 2207/10068* (2013.01); *G06T 2207/20221* (2013.01); *G06T 2207/30196* (2013.01)

(56) References Cited

U.S. PATENT DOCUMENTS

| | | |
|---|---|---|
| 2009/0051695 A1 | 2/2009 | Matsuda et al. |
| 2009/0245692 A1 | 10/2009 | Okutomi et al. |
| 2010/0067808 A1 | 3/2010 | Matsuzaki et al. |
| 2010/0097392 A1 | 4/2010 | Nishiyama et al. |
| 2010/0194992 A1 | 8/2010 | Kouno et al. |
| 2013/0243323 A1* | 9/2013 | Yaguchi ............. G06K 9/00684 382/173 |
| 2014/0376817 A1* | 12/2014 | Yaguchi ............. A61B 1/00009 382/195 |
| 2015/0030254 A1* | 1/2015 | Yaguchi ................ G06T 7/0083 382/209 |
| 2015/0199590 A1* | 7/2015 | Yaguchi ............... G06K 9/4604 382/195 |
| 2015/0199800 A1* | 7/2015 | Yaguchi ................... G06T 5/50 382/128 |
| 2015/0358547 A1* | 12/2015 | Okuhira ................ H04N 5/217 348/208.4 |

FOREIGN PATENT DOCUMENTS

| | | | | |
|---|---|---|---|---|
| JP | 2007257287 A | | 10/2007 | |
| JP | 2009005020 A | | 1/2009 | |
| JP | 2009050321 A | | 3/2009 | |
| JP | 2009508567 A | | 3/2009 | |
| JP | 2010094185 A | | 4/2010 | |
| JP | 2010158308 A | * | 7/2010 | ........... H04N 1/3872 |
| JP | 2010166288 A | | 7/2010 | |
| JP | 2010183290 A | | 8/2010 | |
| WO | 2007032002 A2 | | 3/2007 | |

* cited by examiner $E(1) = E(0) + G(0,1)$
$= 0$
OPTIMUM PRECEDING
SUMMARY IMAGE=0

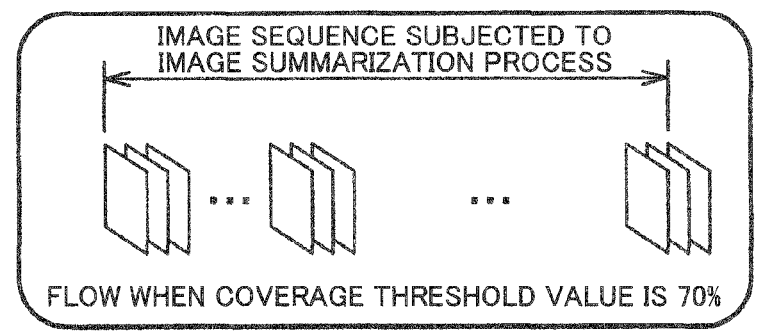
FIG. 10A
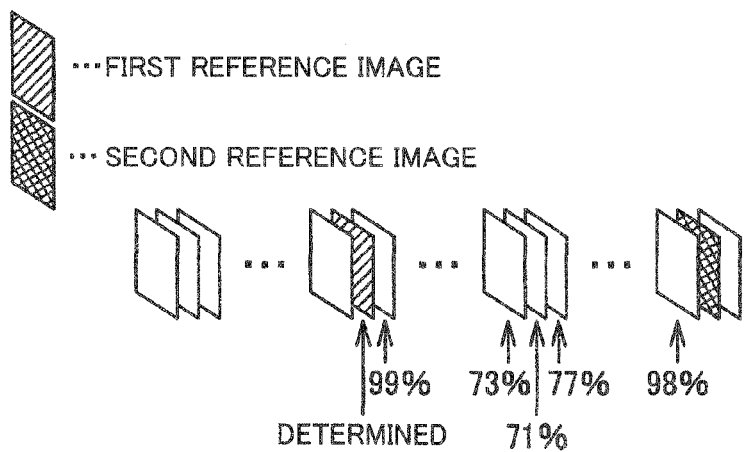
FIG. 10B
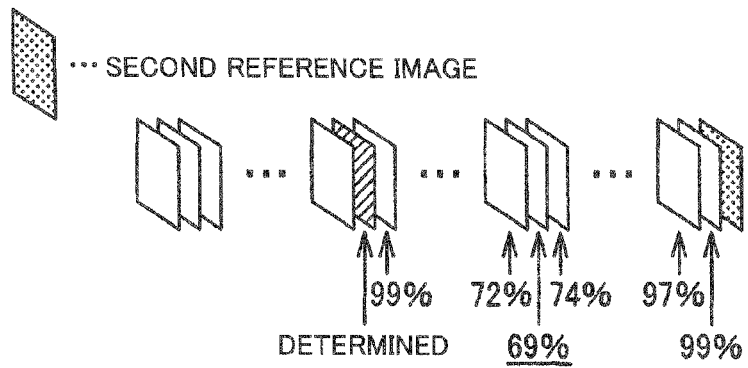

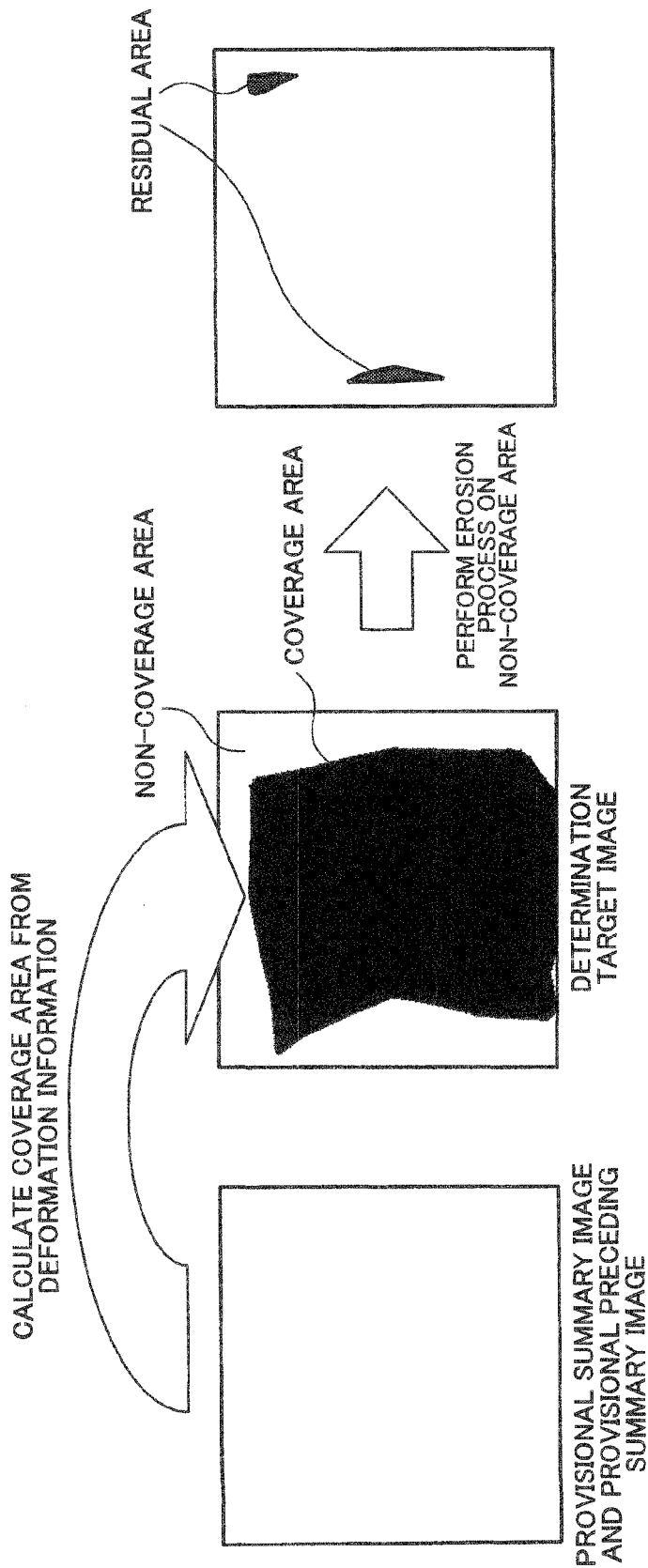

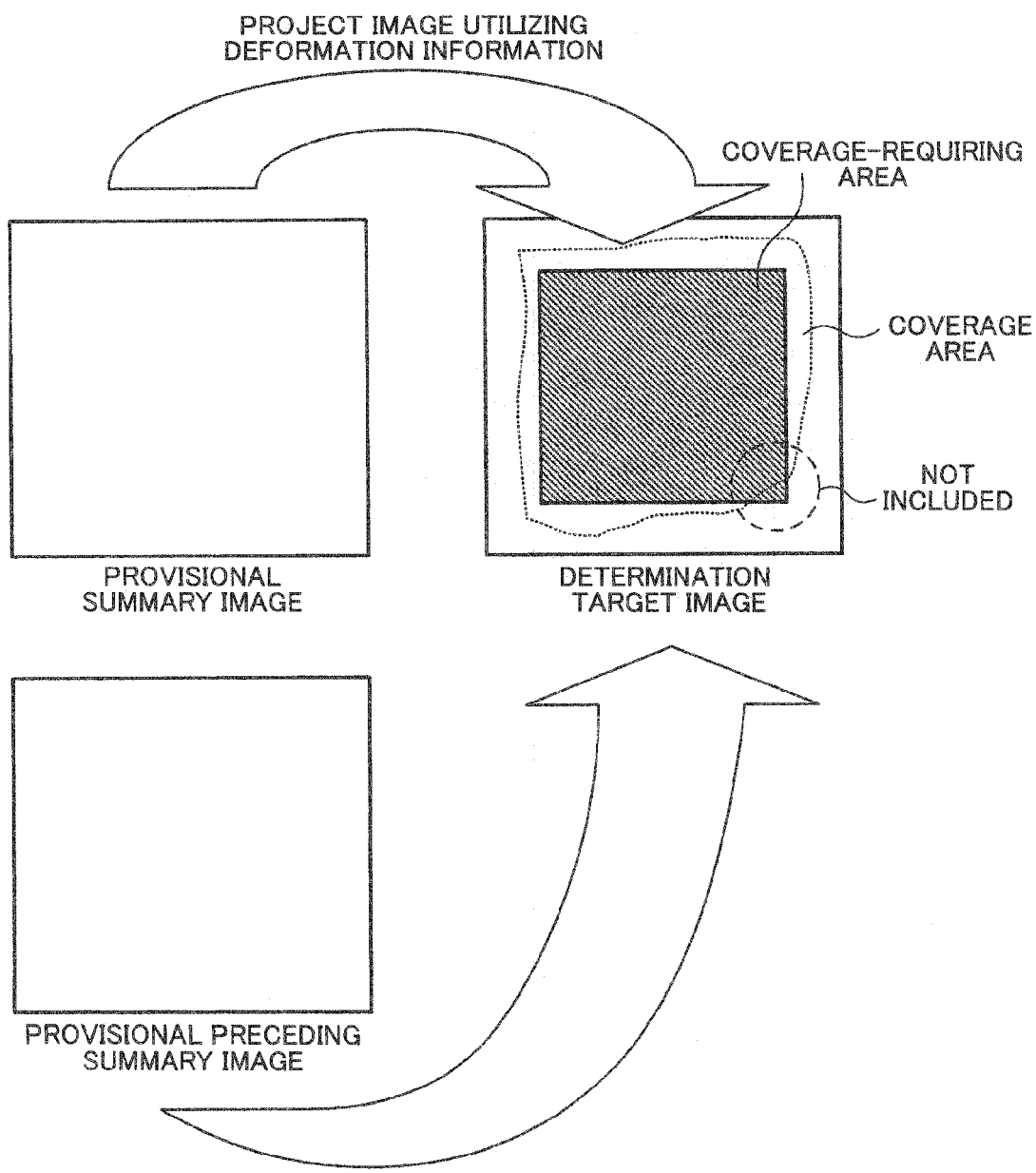

COVERAGE AREA

| COVERAGE / ATTENTION AREA | K1≤COVERAGE (IMAGE CAN BE DELETED) | K2≤COVERAGE<K1 (IMAGE CANNOT BE DELETED) | COVERAGE<K2 (IMAGE CANNOT BE DELETED) |
|---|---|---|---|
| RESIDUAL AREA IS NOT PRESENT (IMAGE CAN BE DELETED) | UPDATE DETERMINATION TARGET IMAGE | G=−∞ | G=−INFINITY AND TERMINATE PROCESS |
| RESIDUAL AREA IS PRESENT (IMAGE CANNOT BE DELETED) | G=−∞ | G=−∞ | G=−INFINITY AND TERMINATE PROCESS |

IMAGE PROCESSING DEVICE, IMAGE PROCESSING METHOD, AND INFORMATION STORAGE DEVICE

CROSS REFERENCE TO RELATED APPLICATION

This application is a continuation of International Patent Application No. PCT/JP2013/084188, having an international filing date of Dec. 20, 2013, which designated the United States, the entirety of which is incorporated herein by reference. Japanese Patent Application No. 2012-287572 filed on Dec. 28, 2012 is also incorporated herein by reference in its entirety.

BACKGROUND

The present invention relates to an image processing device, an image processing method, an information storage device, and the like.

When still images are continuously captured in time series at given time intervals, or when a spatial object is covered by a number of images, or when a movie is captured, and each image included in the movie is used as a still image, for example, a very large number of temporally or spatially continuous images (hereinafter may be referred to as "image sequence") are acquired. In such a case, it is likely that the images that are closely situated within the image sequence (i.e., images that are close to each other temporally or spatially) are similar images, and it is not likely that it is necessary to check all of a large number of images in order to determine the captured information. Since the number of images may typically reach tens of thousands or more, it takes time for the user to check all of the images.

Therefore, it has been desired to summarize the original image sequence using an image sequence that includes a smaller number of images by deleting some of the images from the original image sequence. This process is hereinafter referred to as "image summarization process". For example, JP-A-2009-5020 discloses an image summarization method that extracts a scene change boundary image included in the image sequence, or an image that represents the image sequence, and allows images to remain from which the information represented by the image sequence can be easily determined.

For example, when applying the image summarization technique to the medical field, it is necessary to prevent a situation in which an area that cannot be observed occurs due to deletion of an image in order to prevent a situation in which a disease is missed. In particular, it is necessary to ensure that an important area such as a lesion area or an abnormal area can be reliably observed.

SUMMARY

According to one aspect of the invention, there is provided an image processing device comprising:

an image sequence acquisition section that acquires an input image sequence that includes first to Nth (N is an integer equal to or larger than 2) images as constituent images; and a processing section that performs an image summarization process that deletes some of the first to Nth images included in the input image sequence acquired by the image sequence acquisition section to generate a summary image sequence, the processing section selecting an s-th (s is an integer that satisfies $0 \le s \le N+1$) image included in the input image sequence to be a provisional summary image, selecting a t-th (t is an integer that satisfies $0 \le t \le s-1$) image included in the input image sequence to be a provisional preceding summary image, selecting a u-th (u is an integer that satisfies $t < u < s$) image included in the input image sequence to be a determination target image, calculating a deletion evaluation value of the determination target image based on deformation information about the provisional summary image and the determination target image, and the deformation information about the provisional preceding summary image and the determination target image, calculating a summarization interval evaluation value $G(t, s)$ that is an evaluation value when (t+1)-th to (s−1)-th images are deleted, based on the deletion evaluation values of the (t+1)-th to (s−1)-th images, and performing the image summarization process based on the summarization interval evaluation value.

According to another aspect of the invention, there is provided an image processing method comprising:

acquiring an input image sequence that includes first to N-th (N is an integer equal to or larger than 2) images as constituent images;

selecting an s-th (s is an integer that satisfies $0 \le s \le N+1$) image included in the input image sequence to be a provisional summary image;

selecting a t-th (t is an integer that satisfies $0 \le t \le s-1$) image included in the input image sequence to be a provisional preceding summary image;

selecting a u-th (u is an integer that satisfies $t < u < s$) image included in the input image sequence to be a determination target image;

calculating a deletion evaluation value of the determination target image based on deformation information about the provisional summary image and the determination target image, and the deformation information about the provisional preceding summary image and the determination target image;

calculating a summarization interval evaluation value $G(t, s)$ that is an evaluation value when (t+1)-th to (s−1)-th images are deleted, based on the deletion evaluation values of the (t+1)-th to (s−1)-th images; and performing an image summarization process based on the summarization interval evaluation value, the image summarization process deleting some of the first to N-th images included in the input image sequence to generate a summary image sequence.

According to another aspect of the invention, there is provided an information storage device storing a program that causes a computer to function as:

an image sequence acquisition section that acquires an input image sequence that includes first to N-th (N is an integer equal to or larger than 2) images as constituent images; and a processing section that performs an image summarization process that deletes some of the first to N-th images included in the input image sequence acquired by the image sequence acquisition section to generate a summary image sequence, the processing section selecting an s-th (s is an integer that satisfies $0 \le s \le N+1$) image included in the input image sequence to be a provisional summary image, selecting a t-th (t is an integer that satisfies $0 \le t \le s-1$) image included in the input image sequence to be a provisional preceding summary image, selecting a u-th (u is an integer that satisfies $t < u < s$) image included in the input image sequence to be a determination target image, calculating a deletion evaluation value of the determination target image based on deformation information about the provisional summary image and the determination target image, and the deformation information about the provisional preceding summary image and the determination target image, calculating a summarization interval evaluation value G(t, s) that is an evaluation value when (t+1)-th to (s−1)-th images are deleted based on the deletion evaluation values of the (t+1)-th to (s−1)-th images, and performing the image summarization process based on the summarization interval evaluation value.

BRIEF DESCRIPTION OF THE DRAWINGS

FIGS. 10A and 10B are views illustrating a selection method when using a plurality of reference images.

FIG. 14 is a view illustrating a erosion process that utilizes a structural element, and is performed on a non-coverage area.

FIG. 18 illustrates an example of an inclusion determination process performed on a coverage area and a coverage-requiring area.

DESCRIPTION OF EXEMPLARY EMBODIMENTS

Figure 1:
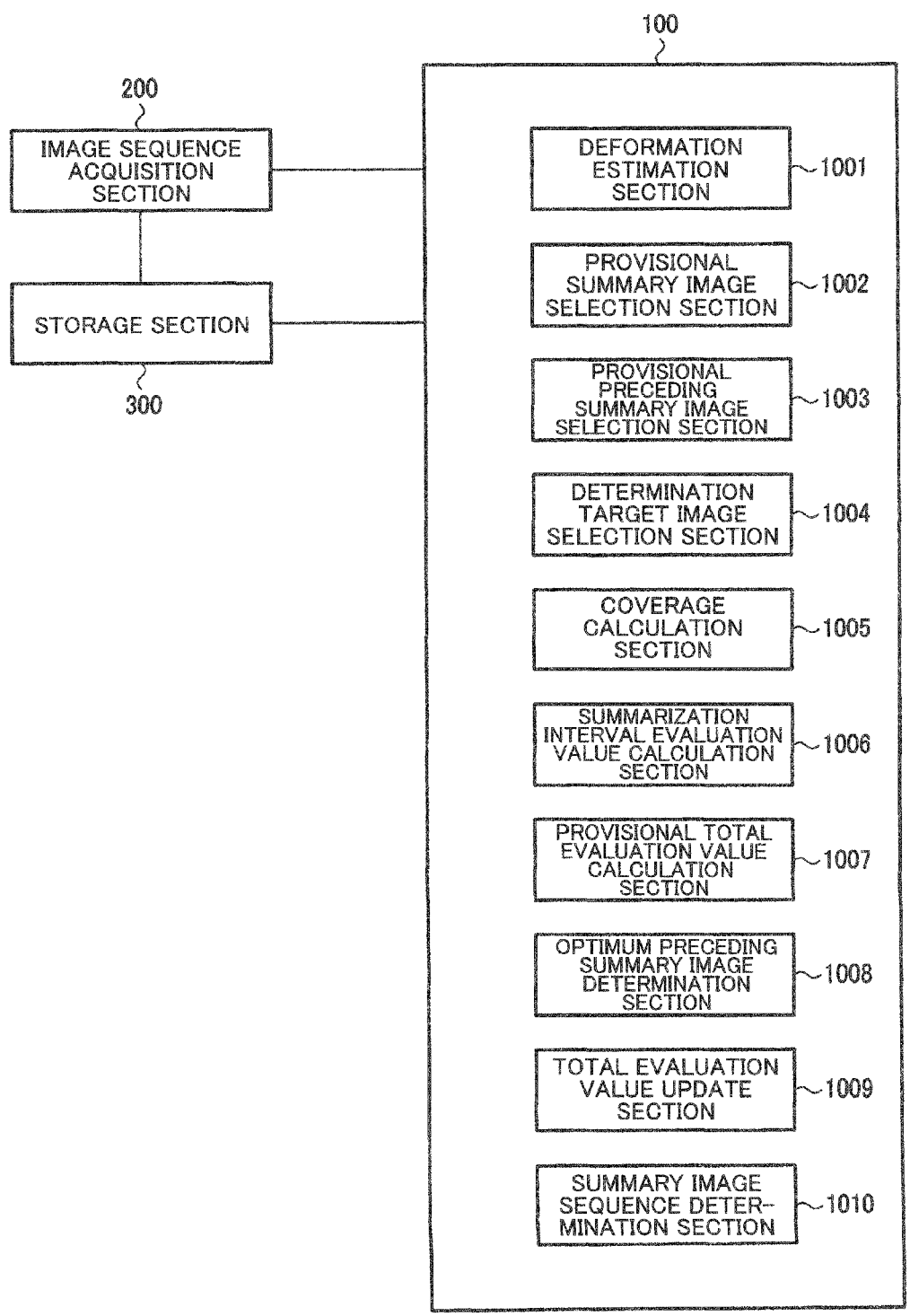
FIG. 1 illustrates a configuration example of an image processing device (first embodiment).

According to one embodiment of the invention, there is provided an image processing device comprising:

an image sequence acquisition section that acquires an input image sequence that includes first to N-th (N is an integer equal to or larger than 2) images as constituent images; and a processing section that performs an image summarization process that deletes some of the first to Nth images included in the input image sequence acquired by the image sequence acquisition section to generate a summary image sequence, the processing section selecting an s-th (s is an integer that satisfies $0 \leq s \leq N+1$) image included in the input image sequence to be a provisional summary image, selecting a t-th (t is an integer that satisfies $0 \leq t \leq s-1$) image included in the input image sequence to be a provisional preceding summary image, selecting a u-th (u is an integer that satisfies $t < u < s$) image included in the input image sequence to be a determination target image, calculating a deletion evaluation value of the determination target image based on deformation information about the provisional summary image and the determination target image, and the deformation information about the provisional preceding summary image and the determination target image, calculating a summarization interval evaluation value G(t, s) that is an evaluation value when (t+1)-th to (s−1)-th images are deleted, based on the deletion evaluation values of the (t+1)-th to (s−1)-th images, and performing the image summarization process based on the summarization interval evaluation value.

According to one embodiment of the invention, the summarization interval evaluation value G(t, s) that is the evaluation value when the (t+1)-th to (s−1)-th images are deleted is calculated, and the image summarization process is performed based on the calculated summarization interval evaluation value. Therefore, when a plurality of candidates for the summary image sequence are present, it is possible to calculate the evaluation value of each candidate by utilizing the summarization interval evaluation value that corresponds to the images deleted from the input image sequence corresponding to each candidate, and determine the optimum summary image sequence (i.e., perform a globally optimized image summarization process) by comparing the evaluation values, for example.

In the image processing device, the processing section may calculate total evaluation values E(1) to E(N) of the first to Nth images based on the summarization interval evaluation value, and may perform the image summarization process based on the total evaluation values.

This makes it possible to implement the image summarization process based on the total evaluation value of each image.

In the image processing device, the processing section may calculate the total evaluation value of a zero-th image that is a virtual image to be E(0)=0, and may calculating the total evaluation value of a v-th (v is an integer that satisfies $1 \leq v \leq N+1$) image by calculating E(v)= max(E(w)+G(w, v)) using the total evaluation value E(w) of a w-th (w is an integer that satisfies $0 \leq w \leq v-1$) image, and the summarization interval evaluation value G(w, v) when (w+1)-th to (v−1)-th images are deleted.

This makes it possible to calculate the total evaluation value of the total evaluation value calculation target image using the total evaluation value of an image that precedes the total evaluation value calculation target image in the image sequence, for example.

In the image processing device, the processing section may select an x-th image that satisfies the following expression (1) to be an optimum preceding summary image the precedes the v-th image.

This makes it possible to calculate the total evaluation value of the processing target image, and calculate the optimum preceding summary image that precedes the processing target image, for example.

In the image processing device,
the processing section may calculate the total evaluation value E(N+1) of an (N+1)-th image that is the virtual image, may set the (N+1)-th image to be a first processing target image during a summary image sequence determination process, may allow the optimum preceding summary image to remain in the summary image sequence, may update the processing target image with the optimum preceding summary image, and may continue the summary image sequence determination process, when the optimum preceding summary image that precedes the processing target image is not the zero-th image, and may terminate the summary image sequence determination process when the optimum preceding summary image that precedes the processing target image is the zero-th image.

This makes it possible to determine the summary image sequence by tracing the optimum preceding summary images from the end point to the start point, for example.

In the image processing device,
the processing section may calculate a coverage of the u-th image based on the deformation information about the s-th image and the u-th image, and the deformation information about the t-th image and the u-th image, the coverage of the u-th image being a ratio in which the u-th image is covered by the s-th image and the t-th image, may calculate the deletion evaluation value based on the coverage, and may calculate a value obtained by adding up the deletion evaluation values of the (t+1)-th to (s−1)-th images to be the summarization interval evaluation value G(t, s) when the (t+1)-th to (s−1)-th images are deleted.

This makes it possible to calculate the summarization interval evaluation value based on the coverage, for example.

In the image processing device,
the processing section may determine whether or not the u-th image can be deleted based on the deformation information about the s-th image and the u-th image, and the deformation information about the t-th image and the u-th image, and may set a first value to be the summarization interval evaluation value G(t, s) when the (t+1)-th to (s−1)-th images are deleted, when it has been determined that at least one constituent image among the (t+1)-th to (s−1)-th images cannot be deleted.

This makes it possible to set a value that is not useful as the summarization interval evaluation value (i.e., a value that prevents a situation in which the t-th image is selected to be the optimum preceding summary image that precedes the s-th image) when the images between the t-th image and the s-th image cannot be sufficiently covered by the t-th image and the s-th image, for example.

In the image processing device,
the processing section may calculate the summarization interval evaluation value G(t, s) when the (t+1)-th to (s−1)-th images are deleted, based on a number of the (t+1)-th to (s−1)-th images, when it has been determined that all of the (t+1)-th to (s−1)-th images can be deleted.

This makes it possible to calculate the summarization interval evaluation value based on the number of images that can be deleted, for example.

In the image processing device,
the processing section may select the t-th image to be the provisional preceding summary image while updating t by −1 from t=s−1 to t=0, may perform a termination determination process based on the deformation information about the t-th image and the u-th image, and the deformation information about the s-th image and the u-th image, may set a first value to be the summarization interval evaluation value G(x, s) when the constituent image between an x-th (x is an integer that satisfies 0≤x≤t) image and the s-th image is deleted, with respect to t for which it has been determined by the termination determination process to terminate a process, and may terminate a process in which the s-th image is selected to be the provisional summary image.

This makes it possible to terminate the provisional preceding summary image update process, and reduce the amount of calculations, for example.

In the image processing device,
the processing section may set the first value to negative infinity, or a value that is equal to or smaller than a given threshold value determined based on the total evaluation value.

This makes it possible to specifically set the first value, for example.

In the image processing device,
the processing section may select (s−α)-th (α is a positive integer) to (s−1)-th images among zero-th to (s−1)-th images to be the provisional preceding summary image.

This makes it possible to limit the number of images that are selected to be the provisional preceding summary image, and reduce the amount of calculations, for example.

In the image processing device,
the processing section may detect a scene change from the input image sequence, may set constituent images among the plurality of constituent images included in the input image sequence that follow an i-th (i is an integer) scene change and precede an (i+1)-th scene change, to be a partial image sequence, when the i-th scene change and the (i+1)-th scene change that follows the i-th scene change have been detected from the input image sequence, and may perform the image summarization process on the partial image sequence.

This makes it possible to perform the process on the partial image sequence that has been set based on the scene change, and reduce the amount of calculations, for example.

According to another embodiment of the invention, there is provided an image processing method comprising:
acquiring an input image sequence that includes first to Nth (N is an integer equal to or larger than 2) images as constituent images;
selecting an s-th (s is an integer that satisfies 0≤s≤N+1) image included in the input image sequence to be a provisional summary image;
selecting a t-th (t is an integer that satisfies 0≤t≤s−1) image included in the input image sequence to be a provisional preceding summary image;
selecting a u-th (u is an integer that satisfies t<u<s) image included in the input image sequence to be a determination target image;
calculating a deletion evaluation value of the determination target image based on deformation information about the provisional summary image and the determination target image, and the deformation information about the provisional preceding summary image and the determination target image;
calculating a summarization interval evaluation value G(t, s) that is an evaluation value when (t+1)-th to (s−1)-th images are deleted, based on the deletion evaluation values of the (t+1)-th to (s−1)-th images; and
performing an image summarization process based on the summarization interval evaluation value, the image summarization process deleting some of the first to Nth images included in the input image sequence to generate a summary image sequence.

Another embodiment of the invention relates to an information storage device storing a program that causes a computer to function as each section described above.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method used in connection with several exemplary embodiments of the invention is described below. It is desirable to perform the image summarization process when an image sequence that includes a large number of temporally or spatially continuous images has been acquired, and the user performs a process (e.g., medical practice (e.g., diagnosis) when the image sequence is an endoscopic image sequence) using the image sequence. This is because the number of images included in the image sequence is very large, and it takes time for the user to check all of the images included in the image sequence to make a determination. Moreover, it is likely that similar images are included in the image sequence, and the amount of information that can be acquired is limited even if such similar images are thoroughly checked.

Specific examples of such an image sequence include an image sequence captured using a capsule endoscope. The capsule endoscope is a capsule-shaped endoscope that includes a small camera, and captures an image at given time intervals (e.g., twice a second). Since the capsule endoscope remains inside a body for several hours (tens or more hours in some cases) until it is discharged from the body, several tens of thousands of captured images are acquired during a single examination. When the capsule endoscope moves inside a living body, the capsule endoscope may stop, or move backward, due to the motion of the living body, for example. Therefore, a large number of captured images may include a number of images that capture a similar object, and are not useful for finding a lesion or the like.

A known image summarization process may extract a scene change boundary image or an image that represents the image sequence. However, such a known image summarization process deletes an image without taking account of the relationship between the object captured within the deletion target image and the object captured within the image that is allowed to remain. Therefore, the object that is captured within an image included in the original image sequence may not be captured within each image included in the image sequence obtained by the image summarization process. Since the degree of occurrence of a situation in which the object that is captured within an image included in the original image sequence is not included in each image included in the image sequence obtained by the image summarization process, depends on the processing target image sequence, it is difficult to control the degree of occurrence of such an object using a known method.

This is particularly undesirable when applying the image summarization process to the medical field. This is because it is necessary to prevent a situation in which the attention area (e.g., lesion) is missed as much as possible. In order to prevent a situation in which the attention area is missed, it is desirable to capture a wide range inside a living body, and prevent a situation in which an object range that cannot be observed occurs due to deletion of a given image during the image summarization process.

In order to solve the above problems, several embodiments of the invention propose a method that selects a reference image (i.e., an image that is allowed to remain (an image that may be allowed to remain depending on the embodiment)) and a determination target image (i.e., a deletion determination target image), and performs the image summarization process based on deformation information about the reference image and the determination target image.

Figure 2:
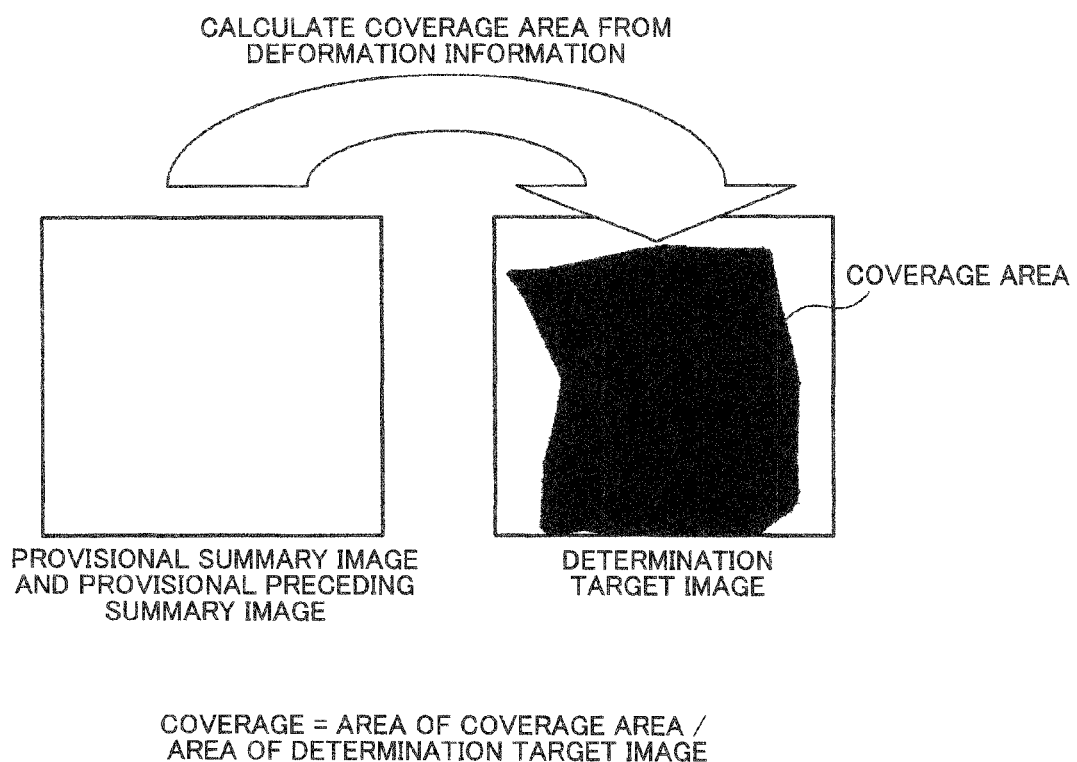
FIG. 2 is a view illustrating a process that utilizes a coverage.

For example, the image summarization process that utilizes the deformation information may calculate a coverage area within the determination target image by deforming the reference image (see FIG. 2). In this case, the object captured within the reference image corresponds to the object captured within the coverage area included in the determination target image. Specifically, an area (hereinafter referred to as "non-coverage area") of the determination target image that is not included in the coverage area cannot be covered by the reference image when the determination target image is deleted.

Therefore, the degree by which an object range that cannot be observed occurs is controlled by calculating the ratio of the coverage area with respect to the determination target image as a coverage, and determining whether or not to delete the determination target image based on the calculated coverage, for example. The determination target image is deleted when the coverage is equal to or larger than a threshold value, and is not deleted when the coverage is less than the threshold value, for example. In this case, the degree by which an area that cannot be covered occurs can be controlled by appropriately setting the threshold value.

The image summarization process that utilizes the deformation information may determine whether or not the determination target image can be deleted based on the results of a erosion process that is performed on the non-coverage area using a structural element (corresponding to an attention area). FIGS. 15A to 15E illustrate the erosion process. The details of the erosion process are described later. In this case, at least part of an area captured within the determination target image having a size equal to or larger than that of the structural element is necessarily captured within the reference image even if the determination target image is deleted. Therefore, when the entire attention area is captured within the determination target image, at least part of the attention area can be observed within the reference image irrespective of the position of the attention area within the determination target image, and a situation in which the attention area is missed can be prevented.

It is possible to reduce the ratio of an area that cannot be covered by the reference image to a value equal to or less than a given value, or suppress a situation in which the attention area is missed, by performing the image summarization process that utilizes the deformation information. However, it is necessary to optimize the resulting summary image sequence from a different point of view. It is desirable that the number of summary images included in the summary image sequence be as small as possible taking account of the subsequent process (e.g., diagnosis performed by a doctor) that utilizes the summary image sequence. When using the coverage, it is desirable that the integrated value of the coverage be large since the ratio of an area that cannot be covered by the reference image is small, for example. Specifically, when a plurality of candidates for the summary image sequence exist, an image sequence in which the number of summary images is smaller, and the integrated value of the coverage is larger than those of the other image sequence(s) should be output as the summary image sequence, for example. However, since the image summarization process that utilizes the deformation information cannot implement such a process, it is necessary to use an optimization method that can implement such a process.

Figure 9A:
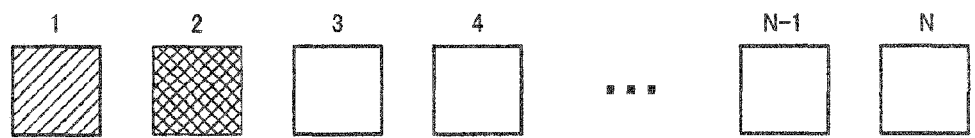
FIGS. 9A to 9C are views illustrating a method for selecting a reference image and determination target image.

As illustrated in FIG. 9A, the image summarization process that utilizes the deformation information may select the first image of the input image sequence that includes N images to be the reference image, and determine whether or not the second or subsequent image (i.e., determination target image) can be deleted, without taking account of optimization of the summary image sequence, for example. In this case, when it has been determined that the second image can be deleted, the determination target image is updated with the third image to search an image that can be deleted (see FIG. 9B). When it has been determined that the second to (k−1)-th images can be deleted, and the k-th image cannot be deleted (see FIG. 9C), the second to (k−1)-th images are sufficiently covered by the first image even if the second to (k−1)-th images are deleted. The k-th image that cannot be covered by the first image is set to the next reference image that is allowed to remain in the summary image sequence.

Figure 9B:
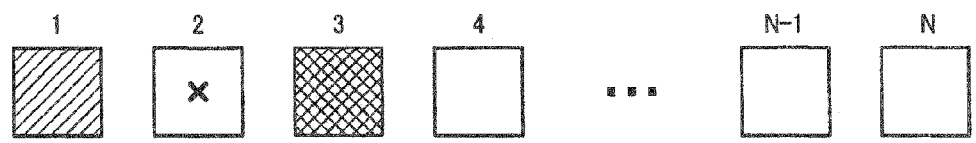
Figure 9C:
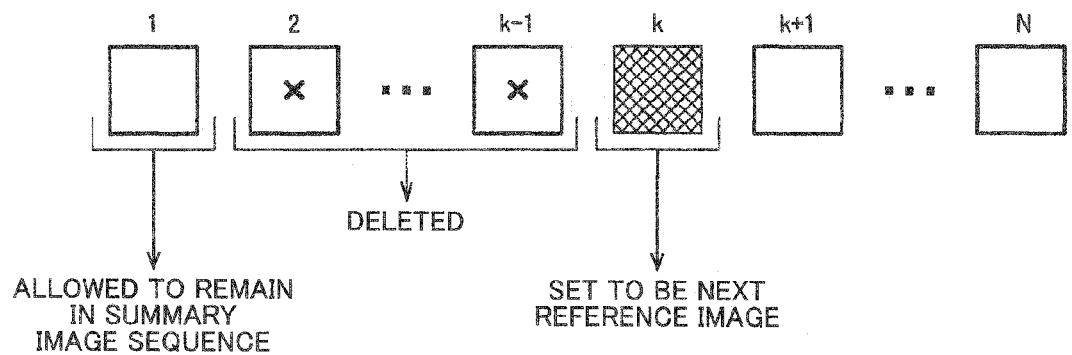

The method illustrated in FIGS. 9A to 9C reduces the number of summary images by setting the next summary image to be situated away from the preceding summary image as much as possible. However, the method illustrated in FIGS. 9A to 9C determines the k-th image to be the summary image taking account of only the first image, and does not take account of the entire input image sequence including the (k+1)-th to Nth images. If the object captured within the (k−1)-th image is similar to the object captured within the (k+1)-th to Nth images as compared with the object captured within the k-th image, it may be possible to increase the degree by which the determination target image is covered by the reference image, and reduce the number of images included in the resulting summary image sequence, by setting the (k−1)-th image to be the summary image.

As illustrated in FIGS. 10A and 10B, it may be possible to improve the effect of reducing the number of images and the like by setting a first reference image and a second reference image, and performing the image summarization process based on the degree (coverage) by which the determination target image is covered by the first reference image and the second reference image. In this case, however, it is impossible to ensure that the optimum reference image is selected taking account of the entire image sequence (in the same manner as the method illustrated in FIGS. 9A to 9C) since the reference image is set taking account of only part of the input image sequence.

In order to solve the above problems, several embodiments of the invention propose a method that calculates a globally optimized summary image sequence based on a summarization interval evaluation value G that is an evaluation value when images within a given interval are deleted. Specifically, when an image sequence that includes first to Nth (N is an integer equal to or larger than 2) images as constituent images has been input, the s-th (s is an integer that satisfies 0≤s≤N+1) image and the t-th (t is an integer that satisfies 0≤t≤s−1) image are set to be the reference image, and a deletion evaluation value when each of the (t+1)-th to (s−1)-th images is set to be the determination target image is calculated from the coverage or the like. The summarization interval evaluation value G(t, s) that is the evaluation value when each of the (t+1)-th to (s−1)-th images is deleted, is calculated based on the deletion evaluation value of each of the (t+1)-th to (s−1)-th images, and the image summarization process is performed based on the summarization interval evaluation value.

In other words, the summarization interval evaluation value G(t, s) is the evaluation value on the assumption that the t-th image and the s-th image are allowed to remain in the summary image sequence as the summary image. Therefore, it is possible to implement the image summarization process that takes account of the entire input image sequence by calculating $_{N+2}C_2=(N+2)(N+1)/2$ summarization interval evaluation values G corresponding to the zero-th to (N+1)-th images (the zero-th image and the (N+1)-th image are virtual images as described later), for example. Note that some of the summarization interval evaluation values G may not be calculated taking account of the amount of calculations and the like. The details thereof are described later.

If all of the summary image sequences are evaluated when determining the optimum summary image sequence from the calculated summarization interval evaluation value G, $2^N$ candidates for the optimum summary image sequence are evaluated using the summarization interval evaluation value G, and the amount of calculations becomes enormous, since it is necessary to determine whether or not to delete each of the first to Nth images. Therefore, the optimum summary image sequence may be determined using dynamic programming.

Figures 20, 21:
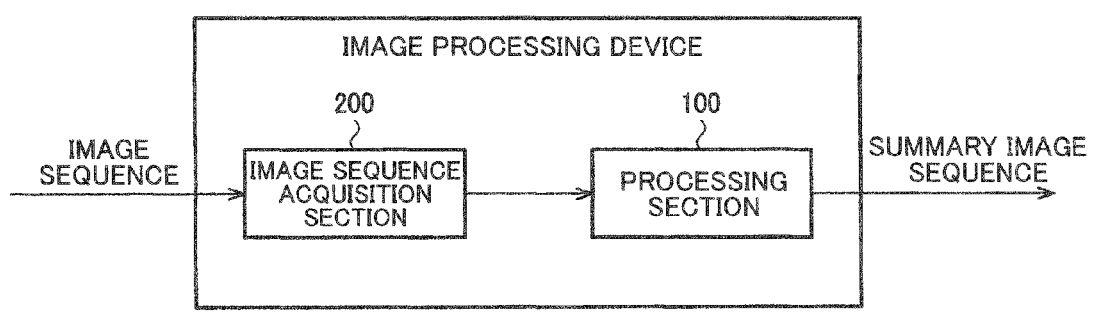
FIG. 20 illustrates a determination process that uses both a coverage and a structural element.
FIG. 21 illustrates a basic configuration example of an image processing device.

An image processing device according to several embodiments of the invention includes an image sequence acquisition section 200 that acquires an image sequence that includes first to Nth (N is an integer equal to or larger than 2) images as constituent images, and a processing section 100 that performs the image summarization process that deletes some of the first to Nth images included in the image sequence acquired by the image sequence acquisition section 200 to generate a summary image sequence (see FIG. 21). The processing section 100 selects an s-th (s is an integer that satisfies 0≤s≤N+1) image included in the input image sequence to be a provisional (temporary or conditional) summary image, selects a t-th (t is an integer that satisfies 0≤t≤s−1) image included in the input image sequence to be a provisional (temporary or conditional) preceding summary image, selects a u-th (u is an integer that satisfies t<u<s) image included in the input image sequence to be the determination target image, calculates the deletion evaluation value of the determination target image based on the deformation information about the provisional summary image and the determination target image, and the deformation information about the provisional preceding summary image and the determination target image, calculates the summarization interval evaluation value G(t, s) that is the evaluation value when the (t+1)-th to (s−1)-th images are deleted based on the deletion evaluation values of the (t+1)-th to (s−1)-th images, and performs the image summarization process based on the summarization interval evaluation value.

A first embodiment illustrates a method that performs a process based on the coverage as the process that utilizes the deformation information. In the first embodiment, the summarization interval evaluation value G is calculated based on the number of images included in the interval (i.e., the number of images that can be deleted when the interval is selected), and the coverage. A second embodiment illustrates a method that performs the erosion process that utilizes the structural element as the process that utilizes the deformation information. In the second embodiment, the summarization interval evaluation value G is calculated based on the number of images included in the interval (i.e., the number of images that can be deleted when the interval is selected). The method according to the first embodiment and the method according to the second embodiment may be combined as a modifications (described later).

2. First Embodiment

The first embodiment illustrates the method that utilizes the coverage. Dynamic programming will be briefly explained first, and a method that applies dynamic programming to the image summarization process will then be described. A system configuration example of the image processing device will be described thereafter, and the flow of the process will then be described using a flowchart. A specific example of the process according to first embodiment will be described thereafter with reference to FIGS. 5A to 8B, and a modification that takes account of a reduction in the amount of calculations will then be described.

2.1 Brief Explanation of Dynamic Programming

Figure 12:
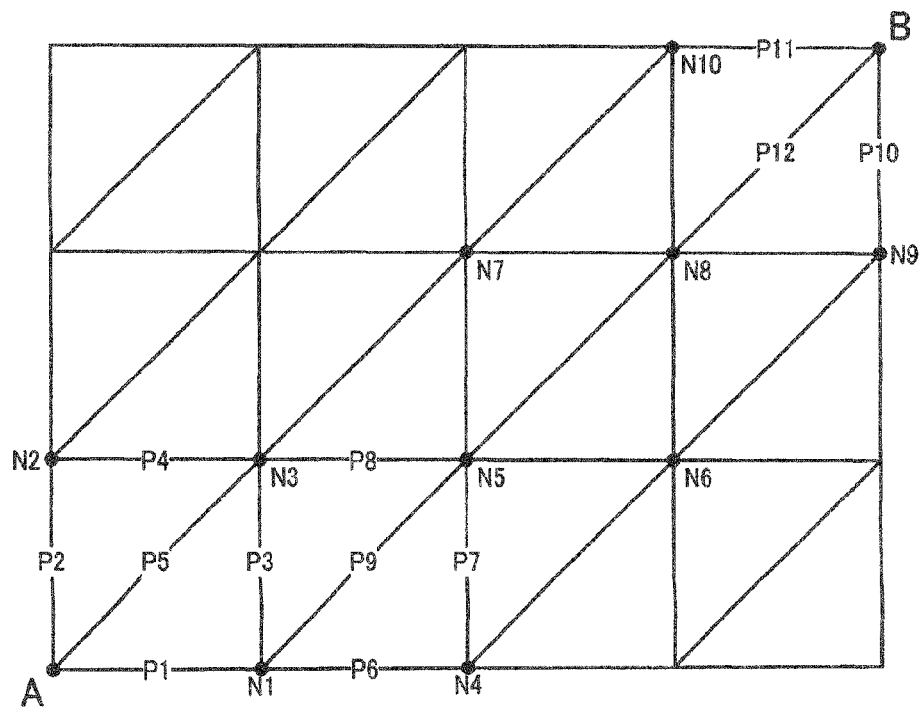
FIG. 12 is a view illustrating dynamic programming.

Dynamic programming is used for various methods (e.g., optimum path search and matching) For example, dynamic programming can be used when calculating the optimum path from the point A to the point B illustrated in FIG. 12. In the example illustrated in FIG. 12, movement from the point A toward the point B occurs in the rightward direction, the upward direction, or the upper right direction, and movement in the backward direction does not occur. An evaluation value (e.g., p1 to p12) for movement through each path (route) is set between each node. Note that a larger evaluation value represents a better evaluation result. In this case, the optimum path from the point A to the point B can be defined to be a path that maximizes the total evaluation value of each branch, for example.

The problem illustrated in FIG. 12 can be solved by calculating the total evaluation value corresponding to all of the paths from the point A to the point B, and determining the path that provides the maximum total evaluation value to be the optimum path. In the example illustrated in FIG. 12, since the distance between the point A and the point B is short, and the number of paths from each node to the next node is limited to 3 or less, the total number of paths is small, and the total evaluation value can be calculated corresponding to all of the paths. However, when the problem is a large-scale problem (e.g., the number of nodes is several tens of thousands when implementing the image summarization process), it is not realistic to integrate the evaluation values corresponding to all of the paths.

Dynamic programming makes it possible to solve such a problem with a realistic amount of calculations. Specifically, the evaluation value (i.e., the largest value among the candidates for the evaluation value) of each node, and the node that precedes each node are determined from the node closest to the point A instead of directly calculating the evaluation value at the point B. The evaluation value of the next node is determined utilizing the evaluation value of each node that has been calculated.

FIG. 12 illustrates a specific example of this process. Since the number of paths from the point A to the point N1 is one, the evaluation value E(N1) of the point N1 is calculated to be p1. Likewise, the evaluation value E(N2) of the point N2 is calculated to be p2. When calculating the evaluation value of the point N3, the path from each preceding node to the point N3 is calculated instead of calculating all of the paths from the point A to the point N3. Specifically, the nodes A, N1, and N2 precede the point N3, and it has been calculated that EA=0, E(N1)=p1, and E(N2)=p2. Therefore, the largest value among the values EA+p5, E(N1)+p3, and E(N2)+p4 is calculated to be the evaluation value of the point N3.

The advantage of dynamic programming is small when calculating the evaluation value of the point N3. However, dynamic programming has a significant advantage as the distance from the start point (point A) to the evaluation calculation target node increases. For example, when calculating all of the paths from the point A to the point N5, it is necessary to calculate the candidates for the evaluation value corresponding to five paths, and compare the calculated values. However, when the evaluation values E(N1), E(N3), and E(N4) have been calculated, the evaluation value E(N5) can be determined by calculating the largest value among the values E(N1)+p9, E(N4)+p7, and E(N3)+p8.

The evaluation value EB of the point B can be determined by performing the above process from the point A toward the point B, and calculating the largest value among the values E(N8)+p12, E(N9)+p10, and E(N10)+p11. Therefore, the amount of calculations can be significantly reduced as compared with the case of directly calculating the evaluation value corresponding to all of the paths from the point A to the point B.

In this case, the optimum path is determined by tracing each preceding point from the point B in reverse order. For example, one of the points N8 to N10 has been determined to be the optimum point (i.e., a point that maximizes the evaluation value EB) that immediately precedes the point B when calculating the evaluation value EB. When the optimum point is the point N8, the path from the point N8 to the point B is determined to be part of the optimum path. One of the points N5 to N7 has been determined to be the optimum point (i.e., a point that maximizes the evaluation value E(N8)) that immediately precedes the point N8. When the optimum point is the point N5, the path from the point N5 to the point B through the point N8 is determined to be part of the optimum path. When the optimum preceding point has reached the point A as a result of repeating this process, the path from the point B to the point A through each optimum preceding point corresponds to the optimum path (in reverse order).

When applying dynamic programming to the image summarization process according to the first embodiment, each image included in the input image sequence is considered to be each node of a path, and a path that passes through only the images that are allowed to remain in the summary image sequence is determined by performing the process on the first image to the last image included in the input image sequence. The image summarization process is considered to be a problem that searches the optimum path.

For example, when the input image sequence includes first to fifth images, a path "1-2-3-4-5" is the optimum path when all of the images are allowed to remain in the summary image sequence, and a path "2-4" is the optimum path when only the second image and the fourth image are allowed to remain in the summary image sequence. Specifically, the optimum summary image sequence can be calculated by dynamic programming by searching the optimum path among $2^5=32$ paths as to whether or not to allow each image to remain in the summary image sequence. If the first image is set to be the start point of the path, and the fifth image is set to be the end point of the path, the first image and the fifth image are necessarily allowed to remain in the summary image sequence. This approach is not appropriate for calculating the optimum solution. Therefore, the method according to the first embodiment sets a virtual zero-th image and a virtual (N+1)-th image when the input image sequence includes N images, wherein the zero-th image is set to be the start point (i.e., the point A illustrated in FIG. 12), and the (N+1)-th image is set to be the end point (i.e., the point B illustrated in FIG. 12).

It is necessary to use the evaluation value (e.g., p1) between the nodes in order to calculate the evaluation value (total evaluation value E) of each point. In the first embodiment, the summarization interval evaluation value G calculated using the deformation information about images is used as the evaluation value between the nodes. Specifically, the summarization interval evaluation value G(2, 4) calculated on the assumption that the second image and the fourth image are allowed to remain in the summary image sequence, and the third image is deleted, may be used as the evaluation value of the branch between a node 2 and a node 4.

2.2 System Configuration Example

FIG. 1 illustrates a system configuration example of the image processing device according to the first embodiment. The image processing device includes a processing section 100, an image sequence acquisition section 200, and a storage section 300.

The processing section 100 performs the image summarization process that deletes some of a plurality of images included in an image sequence acquired by the image sequence acquisition section 200. The function of the processing section 100 may be implemented by hardware such as a processor (e.g., CPU) or an ASIC (e.g., gate array), a program, or the like.

The image sequence acquisition section 200 acquires the image sequence that is subjected to the image summarization process. The image sequence acquired by the image sequence acquisition section 200 may include RGB channel images that are arranged in time series. Alternatively, the image sequence acquired by the image sequence acquisition section 200 may be a spatially continuous image sequence (e.g., an image sequence that includes spatially arranged images that have been captured using imaging devices arranged in a row). Note that the images included in the image sequence are not limited to RGB channel images. Another color space (e.g., Gray channel image) may also be used.

The storage section 300 stores the image sequence acquired by the image sequence acquisition section 200, and serves as a work area for the processing section 100 and the like. The function of the storage section 300 may be implemented by a memory (e.g., RAM), a hard disk drive (HDD), or the like.

The processing section 100 may include a deformation estimation section 1001, a provisional summary image selection section 1002, a provisional preceding summary image selection section 1003, a determination target image selection section 1004, a coverage calculation section 1005, a summarization interval evaluation value calculation section 1006, a provisional total evaluation value calculation section 1007, an optimum preceding summary image determination section 1008, a total evaluation value update section 1009, and a summary image sequence determination section 1010 (see FIG. 1). Note that the configuration of the processing section 100 is not limited to the configuration illustrated in FIG. 1. Various modifications may be made, such as omitting some of the elements illustrated in FIG. 1, or adding other elements. Note that each section illustrated in FIG. 1 is provided in order to describe each subroutine when the image summarization process performed by the processing section 100 is divided into a plurality of subroutines. The processing section 100 does not necessarily include each section illustrated in FIG. 1 as an element.

The deformation estimation section 1001 performs a deformation estimation process on two images to acquire the deformation information. Note that the deformation information represents a shape (range) in which the range captured within one image is captured within the other image. The deformation information may be the deformation parameter disclosed in JP-A-2007-257287, for example. In the first embodiment, the deformation estimation section 1001 acquires the deformation information about the provisional summary image selected by the provisional summary image selection section 1002 and the determination target image selected by the determination target image selection section 1004, and the deformation information about the provisional preceding summary image selected by the provisional preceding summary image selection section 1003 and the determination target image, and calculates the coverage based on the acquired deformation information.

Note that the deformation estimation section 1001 need not necessarily directly calculate the deformation information about the reference image (i.e., provisional summary image or provisional preceding summary image) and the determination target image. For example, the deformation information about contiguous images included in the processing target image sequence may be calculated, and the deformation information about non-contiguous images may be calculated by combining the deformation information about contiguous images. In this case, the deformation information about the reference image and the determination target image is calculated by combining the deformation information (all pieces of deformation information in a narrow sense) about the reference image, the determination target image, and contiguous images between the reference image and the determination target image.

This makes it possible to reduce the processing load when calculating the deformation information. Specifically, the deformation information can be calculated using the method disclosed in JP-A-2007-257287, for example. The processing load is normally very light when combining a plurality of pieces of deformation information as compared with the case of calculating the deformation information from the beginning. For example, when the deformation information is a matrix, the processing load is heavy when calculating the matrix from two pieces of image information, while it is very easy to synthesize a plurality of matrices calculated in advance (since it suffices to calculate the product of the matrices, for example).

For example, when the image sequence acquired by the image sequence acquisition section 200 includes N images, two images can be selected from the image sequence in N×(N−1)/2 combinations. Therefore, when directly calculating the deformation information about the reference image and the determination target image, the heavy-load process that calculates the deformation information from the beginning may be performed $N^2$ times. On the other hand, it suffices to perform the heavy-load process only N−1 times when using the deformation information about contiguous images.

The provisional summary image selection section 1002 selects an image in time series from an image (zero-th image) that is virtually arranged to precede the first image of the image sequence to an image ((N+1)-th image) that is virtually arranged to immediately follow the last image of the image sequence, and sets the selected image to be the provisional summary image. The provisional summary image is an image for which the total evaluation value E is calculated.

The provisional preceding summary image selection section 1003 selects the provisional preceding summary image. The provisional preceding summary image is an image that immediately precedes the provisional summary image, and is a candidate for the summary image. When the total evaluation value E of the provisional preceding summary image has been calculated, a candidate for the total evaluation value of the provisional summary image can be calculated from the total evaluation value E of the provisional preceding summary image, and the summarization interval evaluation value between the provisional preceding summary image and the provisional summary image.

When the k-th image is the provisional summary image, the (k−1)-th image is allowed to remain in the summary image sequence, or the (k−1)-th image is deleted, and the (k−2)-th image is allowed to remain in the summary image sequence, or the (k−1)-th image and the (k−2)-th image are deleted, and the (k−3)-th image is allowed to remain in the summary image sequence, or all of the first to (k−1)-th images are deleted. Specifically, all of the images from the image that immediately precedes the provisional summary image to the zero-th image may be sequentially selected as the provisional preceding summary image when it is desired to take account of each case.

It is considered that it is likely that images that are included in the processing target input image sequence and situated close to each other within the input image sequence are similar images. Specifically, it is likely that the coverage is high (i.e., it is determined that all of the images between the provisional summary image and the provisional preceding summary image can be deleted) when the provisional summary image and the provisional preceding summary image are situated close to each other as compared with the case where the provisional summary image and the provisional preceding summary image are situated away from each other. When it has been determined that at least one image among the images between the provisional summary image and the provisional preceding summary image cannot be deleted, and the coverage of the at least one image is very low, the process may be terminated without setting an image that is situated further away from the provisional summary image to be the provisional preceding summary image (as described later). Therefore, the provisional preceding summary image selection section 1003 selects the image that immediately precedes the provisional summary image to be the first provisional preceding summary image, and sequentially updates the provisional preceding summary image with the image that immediately precedes the current provisional preceding summary image, taking account of the processing efficiency.

The determination target image selection section 1004 sequentially selects the images between the provisional summary image and the provisional preceding summary image to be the determination target image. The determination target image selection section 1004 selects the image that immediately precedes the provisional summary image to be the first determination target image, and sequentially updates the determination target image from (with) the image that immediately precedes the current determination target image until the image that immediately follows the provisional preceding summary image is reached.

Figure 3:
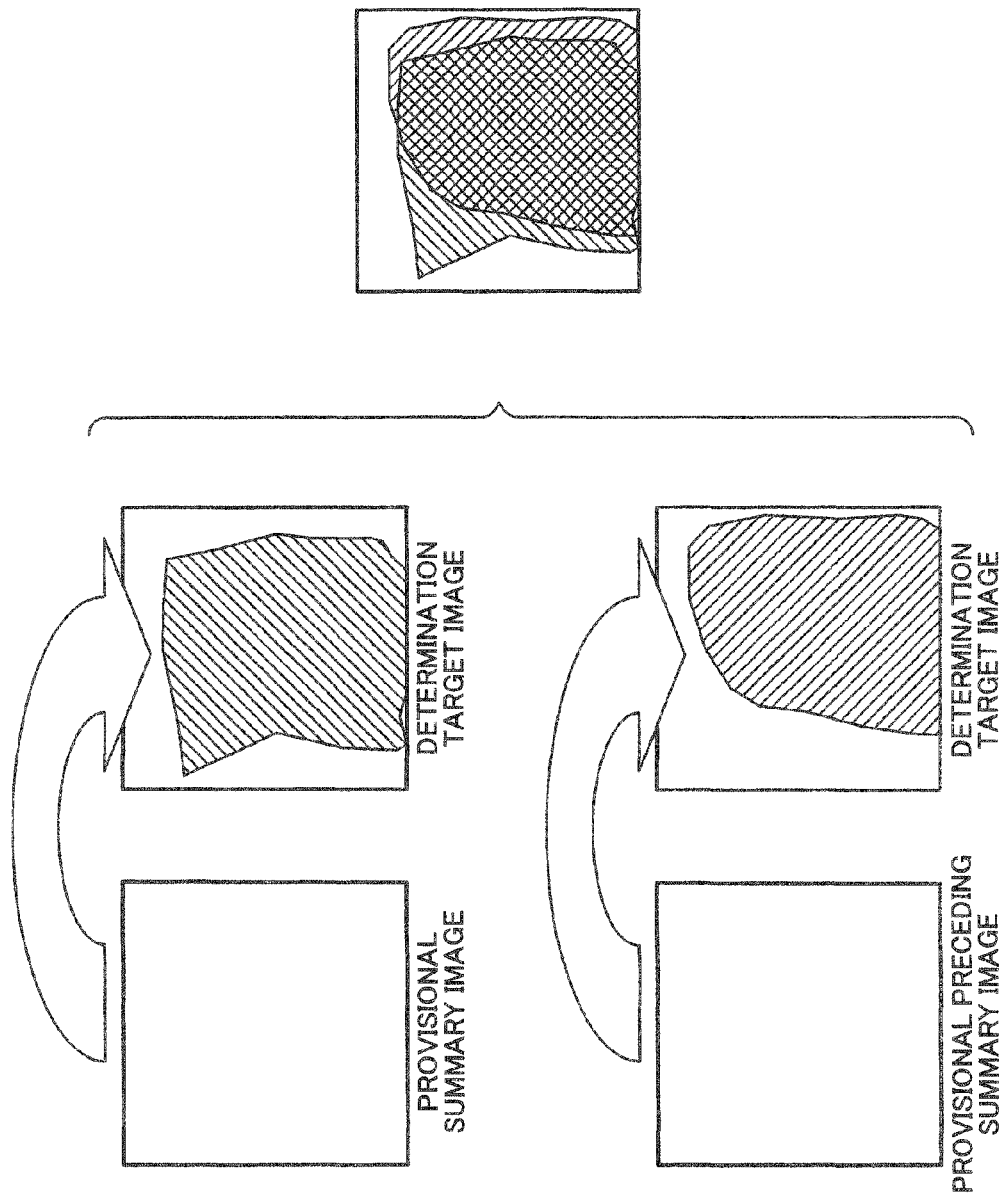
FIG. 3 is a view illustrating a process that utilizes a coverage.

The coverage calculation section 1005 calculates the coverage of the determination target image based on first deformation information about the provisional summary image and the determination target image, and second deformation information about the provisional preceding summary image and the determination target image. FIGS. 2 and 3 illustrate an example of the coverage calculation process. As illustrated in FIG. 3, the provisional summary image is deformed using the first deformation information, and projected onto the determination target image to calculate a first coverage area. The provisional preceding summary image is deformed using the second deformation information, and projected onto the determination target image to calculate a second coverage area. The sum area of the first coverage area and the second coverage area (i.e., an area that is included in at least one of the first coverage area and the second coverage area) is determined to be the final coverage area. The ratio of the coverage area to the determination target image (i.e., the area ratio of the coverage area to the determination target image in a narrow sense) is used as the coverage.

When the coverage of each determination target image is equal to or larger than a threshold value k1, the summarization interval evaluation value is calculated using the coverage. When the coverage of at least one determination target image is less than the threshold value k1, it is not appropriate to delete all of the images between the provisional summary image and the provisional preceding summary image while allowing the provisional summary image and the provisional preceding summary image to remain in the summary image sequence. Therefore, the summarization interval evaluation value is set to a sufficiently small value (e.g., −∞) without calculating a specific value so that such a summary image sequence is not selected (i.e., such a path is not determined to be the optimum path). When the coverage is less than a value k2 (k1>k2), the degree of coverage of the image between the provisional summary image and provisional preceding summary image is very low. In this case, it is considered that it is not likely that the image between the provisional summary image and provisional preceding summary image can be covered even if the provisional preceding summary image is updated with the image that is situated further away from the provisional summary image. In such a case, not only the determination target image update process, but also the provisional preceding summary image update process may be terminated, and the provisional summary image update process may be performed. The details of this branching process is described later with reference to FIG. 4 (flowchart).

The summarization interval evaluation value calculation section 1006 calculates the summarization interval evaluation value based on the coverage, and the number of images between the provisional preceding summary image and the provisional summary image. This is because it is considered that an appropriate summary image sequence can be obtained when the number of images that can be deleted is large, and the coverage is high (see above). Specifically, a first evaluation value is calculated from the total coverage of the determination target images, and the number of images between the provisional preceding summary image and the provisional summary image is calculated to be a second evaluation value. The weighted sum of the first evaluation value and the second evaluation value is then calculated to calculate the summarization interval evaluation value. For example, when the coverage is represented by a value within the range from 0 to 1, a value calculated by "G=(first evaluation value)+(second evaluation value)×(total number of images included in image sequence)" may be used as the summarization interval evaluation value G. In this case, since the weight (total number of images included in image sequence) is large, it is possible to determine the optimum summary image sequence while attaching importance to the number of images that are deleted. Note that the summarization interval evaluation value calculation method is not limited thereto.

The provisional total evaluation value calculation section 1007 calculates the provisional total evaluation value (i.e., a value that is a candidate for the total evaluation value) of the provisional summary image. Specifically, the sum of the total evaluation value of the provisional preceding summary image, and the summarization interval evaluation value calculated corresponding to the provisional summary image and the provisional preceding summary image, is used as the provisional total evaluation value. Since the total evaluation value of the zero-th image is 0, the provisional total evaluation value is equal to the summarization interval evaluation value when the provisional preceding summary image is the zero-th image.

The optimum preceding summary image determination section 1008 determines the provisional preceding summary image that gives the optimum provisional total evaluation value (i.e., the largest provisional total evaluation value in a narrow sense) among one or more provisional total evaluation values calculated by the provisional total evaluation value calculation section 1007, to be the optimum preceding summary image.

The total evaluation value update section 1009 determines the optimum provisional total evaluation value (i.e., the largest provisional total evaluation value in a narrow sense) to be the total evaluation value of the provisional summary image.

The summary image sequence determination section 1010 sets the summary image sequence by tracing the optimum preceding summary images after the total evaluation value E(N+1) of the (N+1)-th image has been calculated. Specifically, when the (N+1)-th image is the first processing target image, and the optimum preceding summary image that precedes the processing target image is not the zero-th image, the optimum preceding summary image is allowed to remain in the summary image sequence, and set to be the next processing target image. When the optimum preceding summary image is the zero-th image, the summary image sequence determination process is terminated. This makes it possible to implement the process that traces the optimum preceding summary image from the (N+1)-th image to the zero-th image to generate a summary image sequence that includes the images (nodes) that form the path.

2.3 Details of Process

Figure 4:
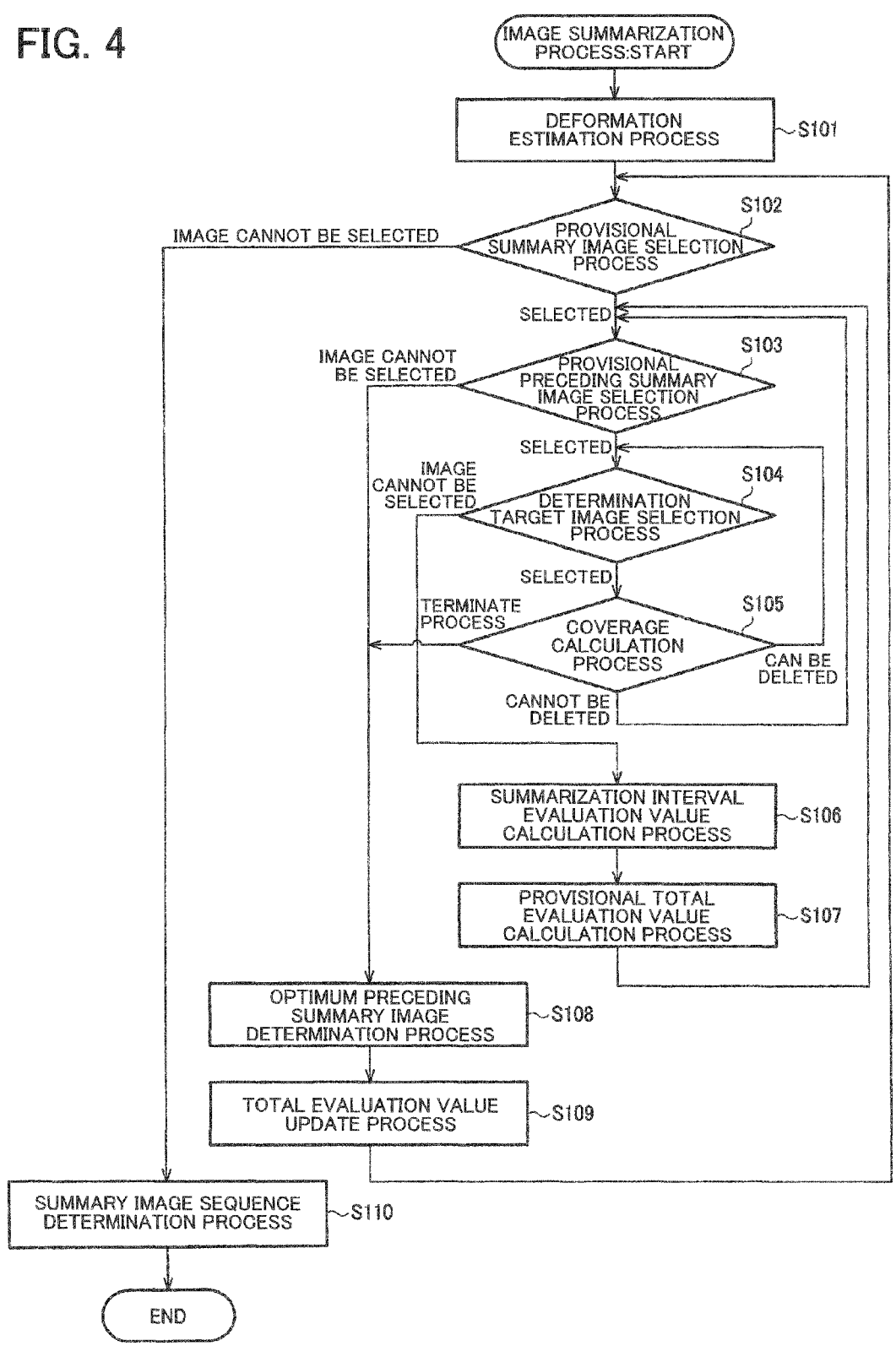
FIG. 4 is a flowchart illustrating an image summarization process (first embodiment).

The flow of the image summarization process according to the first embodiment is described below with reference to FIG. 4 (flowchart). The deformation estimation process is performed in the step S101. For example, the deformation estimation process acquires the deformation information about contiguous images included in the input image sequence.

The provisional summary image is then selected (S102). When the step S102 is performed for the first time, the zero-th image (i.e., virtual image) is selected to be the provisional summary image. When the step S102 is performed thereafter, the provisional summary image is updated with the image that immediately follows the current provisional summary image within the input image sequence.

When the provisional summary image has been selected, the provisional preceding summary image is selected (S103). Specifically, the image that immediately precedes the provisional summary image is selected to be the provisional preceding summary image. When the step S103 has been performed again (after the step S105 or S107) without the step S102 (provisional summary image update process) having been performed, the provisional preceding summary image is updated with the image that immediately precedes the current provisional preceding summary image.

When the provisional summary image and the provisional preceding summary image have been selected, the images between the provisional summary image and the provisional preceding summary image are sequentially selected to be the determination target image (S104). When the determination target image has been selected, the coverage is calculated using the first deformation information about the provisional summary image and the determination target image, and the second deformation information about the provisional preceding summary image and the determination target image (S105). The first deformation information and the second deformation information may be calculated using the results of the deformation estimation process performed in the step S101.

When it has been determined that the determination target image can be deleted based on the coverage (e.g., when the coverage is equal to or larger than the threshold value k1), the determination target image is updated in the step S104. The steps S104 and S105 are repeated as long as the determination target image can be deleted, and the process is performed on all of the images between the provisional summary image and the provisional preceding summary image.

When it has been determined that all of the images between the provisional summary image and the provisional preceding summary image can be deleted, the summarization interval evaluation value is calculated (S106), and the provisional total evaluation value of the provisional summary image is calculated based on the summarization interval evaluation value and the total evaluation value of the provisional preceding summary image (S107). The provisional preceding summary image is then updated in the step S102.

When it has been determined that at least one image among the images between the provisional summary image and the provisional preceding summary image cannot be deleted, and it has not been determined to terminate the process (e.g., when k2≤coverage<k1), it is determined that the images between the provisional summary image and the provisional preceding summary image cannot be sufficiently covered using the current combination of the provisional summary image and the provisional preceding summary image. Therefore, the summarization interval evaluation value is set to a sufficiently small value (e.g., $-\infty$) so that the current combination of the provisional summary image and the provisional preceding summary image is not employed as the summary image. However, since the coverage is a moderate value, and it has not been determined to terminate the process, the provisional preceding summary image is updated in the step S103. It is normally likely that it is determined that the determination target image cannot be deleted as the number of images between the provisional summary image and the provisional preceding summary image increases. On the other hand, the degree of coverage of the images between the provisional summary image and the provisional preceding summary image may increase depending on the object and the like as the number of images between the provisional summary image and the provisional preceding summary image increases.

When the coverage of the determination target image is very small (e.g., when the coverage is less than k2), it is considered that the images between the provisional summary image and the provisional preceding summary image cannot be sufficiently covered using the current combination of the provisional summary image and the provisional preceding summary image, and it is not likely that the coverage increases even if the update process that increases the number of images between the provisional summary image and the provisional preceding summary image is performed. Therefore, the loop process (S103 to S107) is terminated, and the step S108 is performed. In this case, the summarization interval evaluation value of the image that is included in the search interval of the provisional preceding summary image, and has not been selected to be the provisional preceding summary image in the step S103 may be set to a sufficiently small value, taking account of the process performed in the step S108 and subsequent step. For example, when it has been scheduled to select the (k−1)-th image to the zero-th image to be the provisional preceding summary image, but it has been determined to terminate the process when the (k−z)-th image has been selected, the summarization interval evaluation value is not set when the (k−z−1)-th image to the zero-th image are selected to be the provisional preceding summary image. Therefore, the summarization interval evaluation value may be set to −∞.

When the provisional preceding summary image has been repeatedly updated in the step S103, and the search process has been performed over the entire search interval, the step S108 is performed. This state refers to a state in which all of the images including the image that immediately precedes the provisional summary image to the zero-th image have been selected to be the provisional preceding summary image, and the process has been performed, for example. When the number of images that are selected to be the provisional preceding summary image is limited to α in order to reduce the amount of calculations, the above state refers to a state in which α images have been selected to be the provisional preceding summary image sequentially from the image that immediately precedes the provisional summary image, and the process has been performed.

The provisional total evaluation value (i.e., the total evaluation value when one more provisional preceding summary image or each of a plurality of provisional preceding summary images has been set to be the preceding summary image with respect to the provisional summary image selected in the step S102) has been calculated when the step S108 is performed. Therefore, the provisional preceding summary image that gives the optimum provisional total evaluation value (i.e., the largest provisional total evaluation value in a narrow sense) is determined to be the optimum preceding summary image (S108), and the evaluation value is determined to be the total evaluation value of the provisional summary image (S109).

The total evaluation value of the provisional summary image selected in the S102 can be calculated by appropriately repeating the steps S103 to S109. The provisional summary image is updated (S102) after the step S109, and the steps S103 to S109 are repeated to calculate the total evaluation value corresponding to all of the zero-th to (N+1)-th images.

When the total evaluation value of the (N+1)-th image has been calculated (i.e., when the provisional summary image cannot be selected in the step S102), the summary image sequence determination process (S110) is performed. Specifically, a path is selected that starts from the (N+1)-th image, and sequentially traces the optimum preceding summary image that precedes the processing target image up to the zero-th image. The process according to the first embodiment determines the image sequence that includes the images along the path (excluding the zero-th image and the (N+1)-th image (virtual images)) to be the summary image sequence.

2.4 Specific Example of Process

A specific example of the process according to the first embodiment is described below with reference to FIGS. 5A to 8B. The following description illustrates an example in which an image sequence that includes first to sixth images has been input. The numerals 0 to 7 in the lower part of FIGS. 5A to 8B represent the constituent images included in the input image sequence, and the numeral(s) under each of the numerals 0 to 7 represent(s) the total evaluation value of the corresponding image. The value assigned to each intersection of the lattice illustrated in FIGS. 5A to 8B represents the summarization interval evaluation value between two images respectively situated at the lower right and the lower left of the intersection. The thick straight line represents a path from the provisional summary image to the zero-th image through the optimum preceding summary image(s).

Figure 5A:
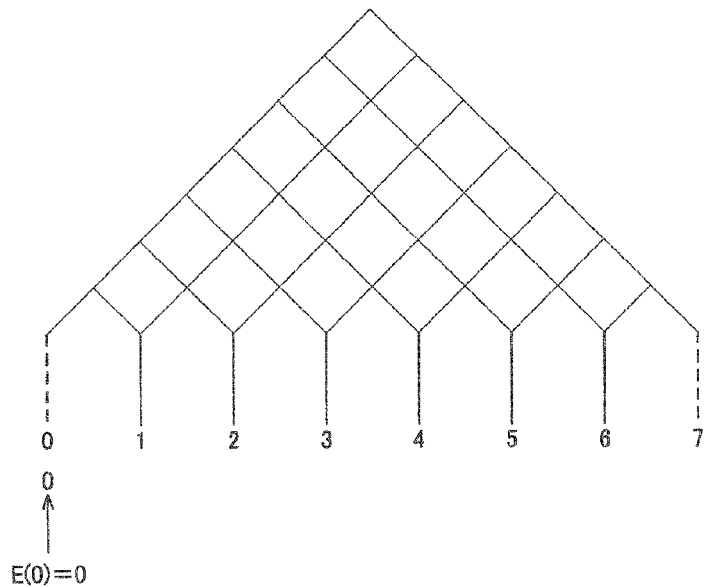
FIGS. 5A and 5B illustrate a specific example of an image summarization process.

As illustrated in FIG. 5A, the total evaluation value E(0) of the zero-th image is 0.

Figure 5B:
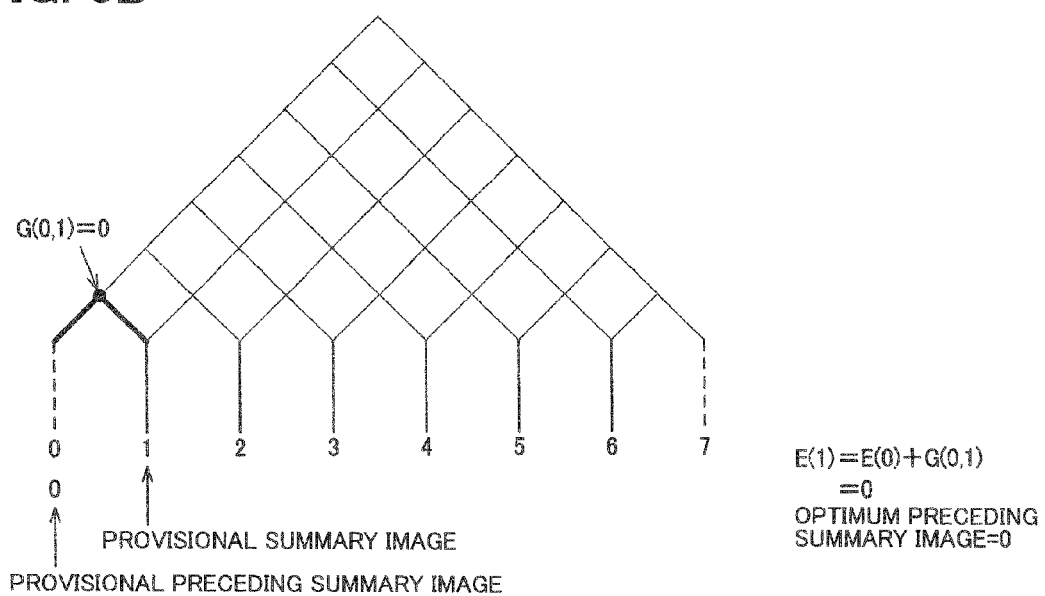

As illustrated in FIG. 5B, the first image is selected to be the provisional summary image, and the image that precedes the first image is selected to be the provisional preceding summary image. In FIG. 5B, the zero-th image is selected to be the provisional preceding summary image, and the summarization interval evaluation value G(0, 1) between the zero-th image and the first image is calculated. In this case, the determination target image is not selected since no image is present between the zero-th image and the first image. Since an image other than the zero-th image is not selected to be the provisional preceding summary image, the zero-th image is determined to be the optimum preceding summary image (E(1)=E(0)+G(0,1)=0).

Figure 6A:
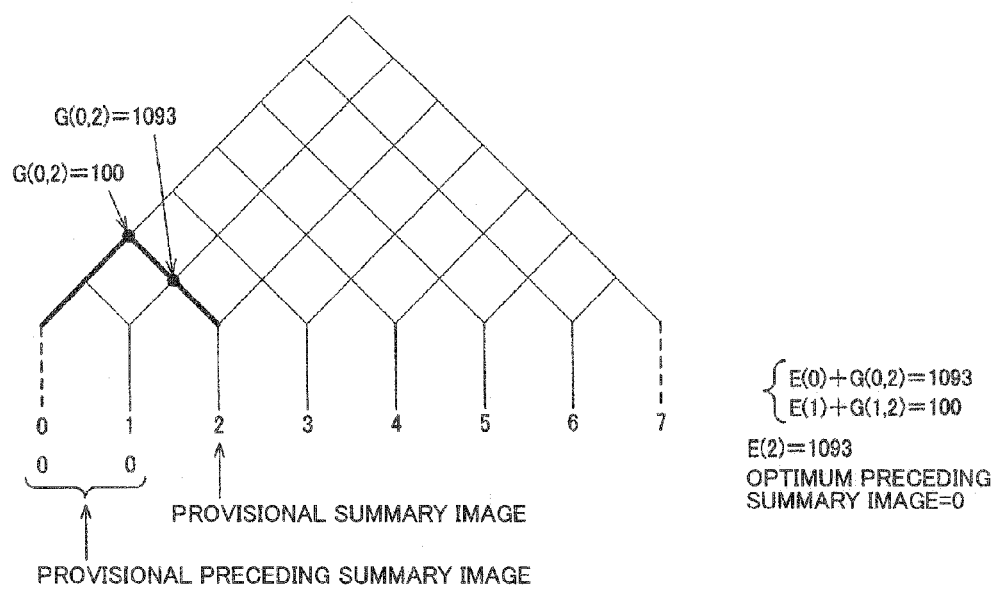
FIGS. 6A and 6B illustrate a specific example of an image summarization process.
Figure 6B:
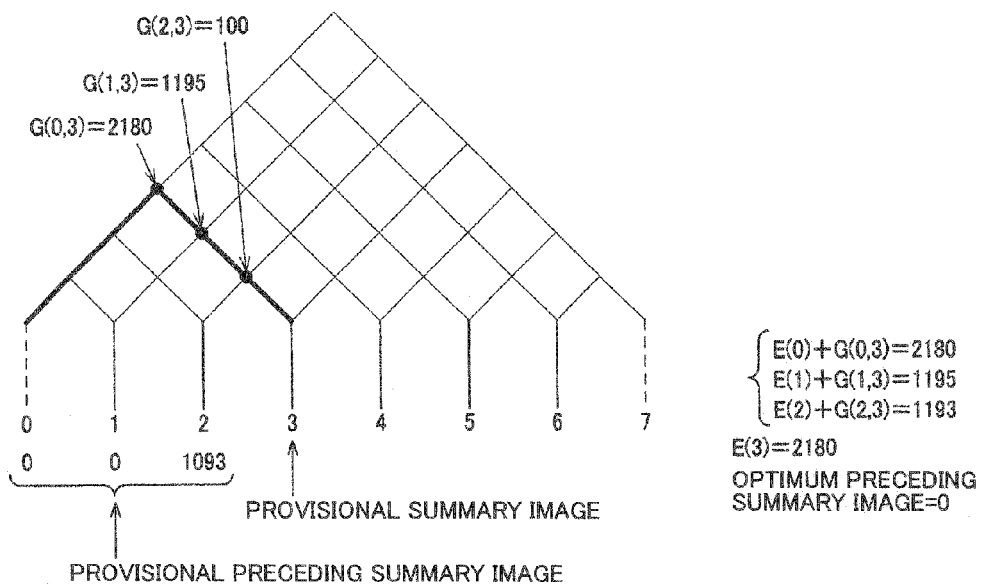

As illustrated in FIG. 6A, the provisional summary image is updated with the second image. The first image is selected to be the provisional preceding summary image, and the summarization interval evaluation value G(1, 2) is calculated. The zero-th image is selected to be the provisional preceding summary image, and the summarization interval evaluation value G(0, 2) is calculated. The first image is selected to be the determination target image when calculating the summarization interval evaluation value G(0, 2).

The provisional total evaluation values "E(1)+G(1, 2)" and "E(0)+G(0, 2)" are calculated, the optimum provisional total evaluation value is determined to be the total evaluation value E(2), and the provisional preceding summary image that gives the optimum provisional total evaluation value is determined to be the optimum preceding summary image. In this case, the total evaluation value E(2) is 1093, and the zero-th image is determined to be the optimum preceding summary image.

Likewise, when the third image has been selected to be the provisional summary image, the second to zero-th images are sequentially selected to be the provisional preceding summary image. When one image or a plurality of images are present between the provisional summary image and the provisional preceding summary image, the one image is selected to be the determination target image, or the plurality of images are sequentially selected to be the determination target image, and the coverage is calculated to calculate the summarization interval evaluation value G. Since the provisional total evaluation values are calculated in a number (three in FIG. 6B) corresponding to the number of images selected to be the provisional preceding summary image, the optimum provisional total evaluation value is determined to be the total evaluation value E(3), and the zero-th image that gives the optimum provisional total evaluation value is determined to be the optimum preceding summary image.

Figure 7A:
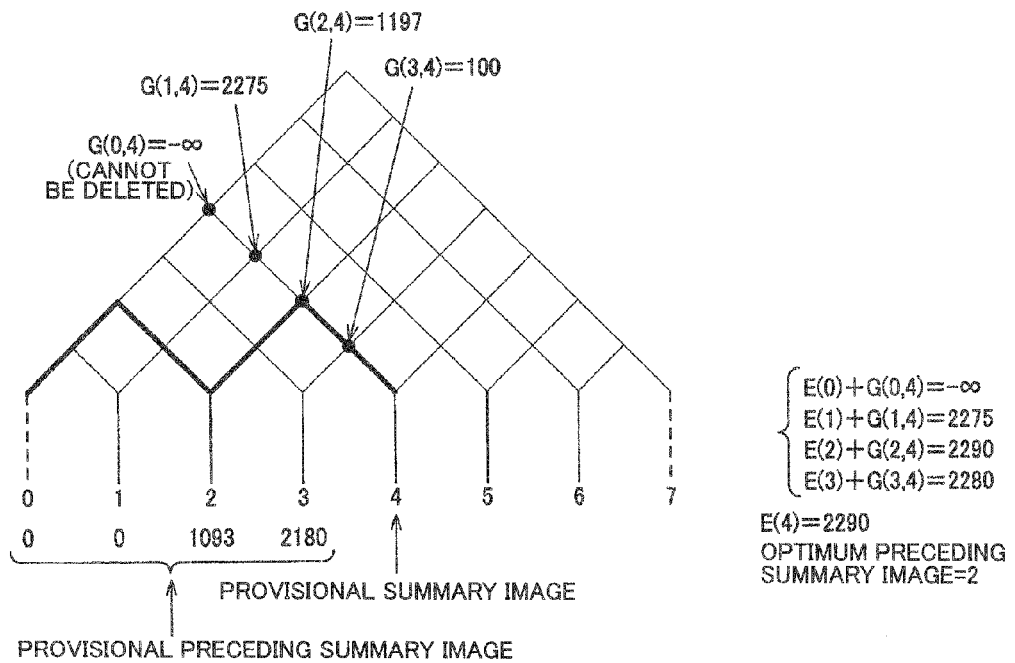
FIGS. 7A and 7B illustrate a specific example of an image summarization process.
Figure 7B:
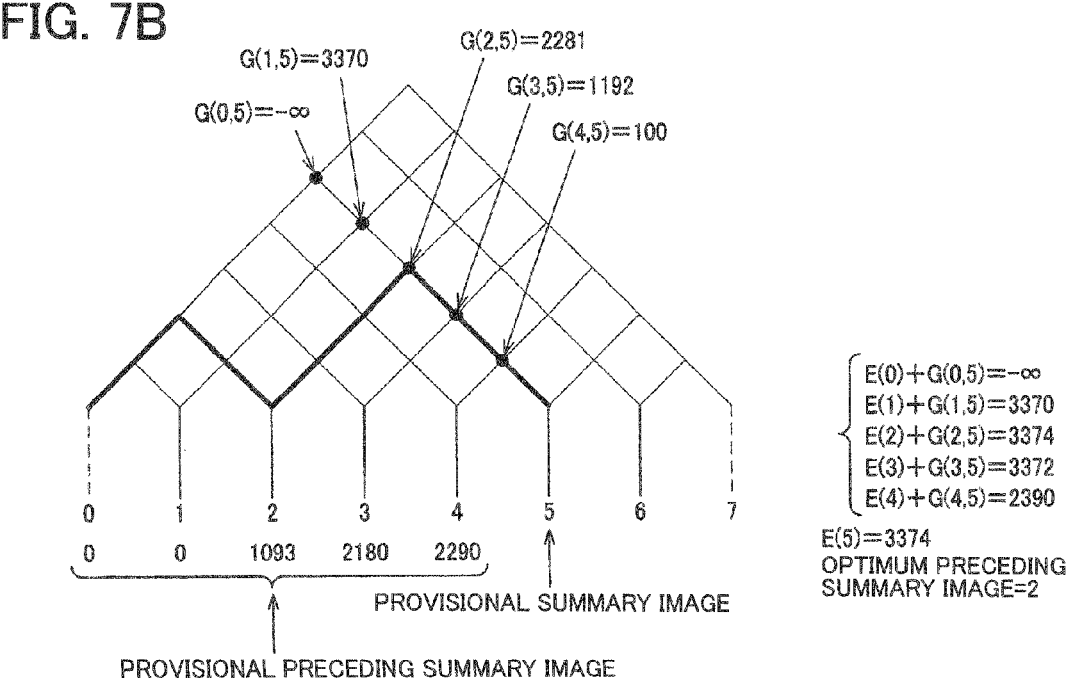

The above description also applies to FIGS. 7A to 8A. In FIG. 7A, since one of the first to third images cannot be deleted (i.e., the coverage is less than a given threshold value when one of the first to third images is selected to be the determination target image) when the zero-th image has been selected to be the provisional preceding summary image, the summarization interval evaluation value G(0, 4) is −∞. Since the optimum preceding summary image is not the zero-th image, it is possible to further determine the optimum preceding summary image.

Figure 8A:
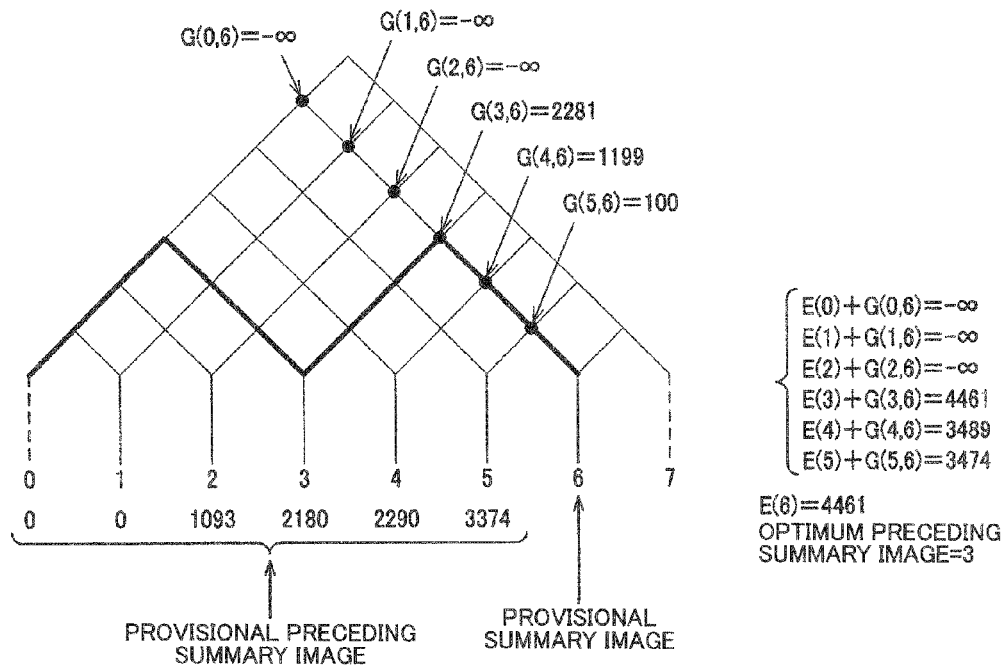
FIGS. 8A and 8B illustrate a specific example of an image summarization process.
Figure 8B:
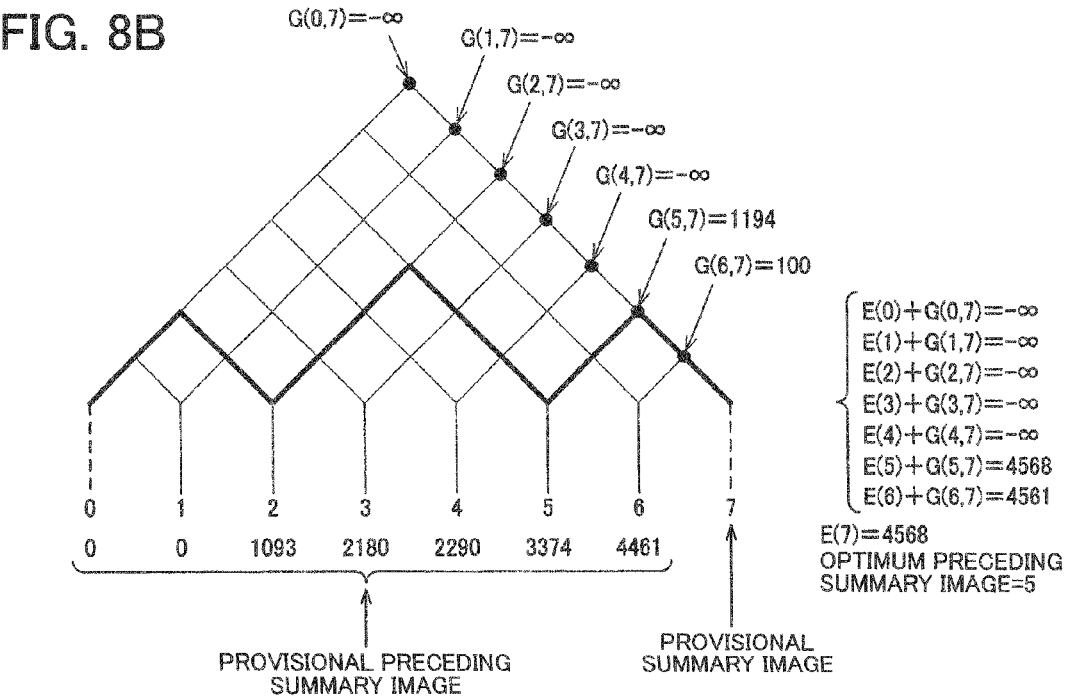

The above process is repeated, and the total evaluation value (E(7) in FIG. 8B) of the virtual image that is set to follow the last image of the input image sequence is calculated. Since the optimum preceding summary image that precedes the seventh image is the fifth image, the optimum preceding summary image that precedes the fifth image is the second image, and the optimum preceding summary image that precedes the second image is the zero-th image, the optimum path from the zero-th image to the seventh the image is calculated to be "0-2-5-7" (see FIG. 8B). Since the zero-th image and the seventh image are virtual images, the optimum summary image sequence of the input image sequence that includes the first to sixth images is determined to be an image sequence that includes the second image and the fifth image.

2.5 Modifications

The process described above with reference to FIG. 4 (flowchart) and the like uses the input image sequence as the image sequence subjected to the image summarization process. However, it is known that the processing time of dynamic programming increases in proportion to the second power of the processing interval length (e.g., a value determined by the path length (determined by the number of images included in the input image sequence in the first embodiment)). Specifically, when the number of images included in the image sequence that is subjected to the image summarization process is very large, it may be difficult to calculate the optimal solution within a realistic processing time even if dynamic programming is used.

In order to reduce the processing time, the image sequence may be divided into a plurality of partial image sequences, and the above process may be performed using each partial image sequence as the input image sequence. This makes it possible to reduce the processing interval length, and reduce the entire processing time.

For example, a scene change may be detected from the image sequence, and the image sequence may be divided into a plurality of partial image sequences based on the detected scene change. A scene change may be detected using various methods. For example, a deformation estimation process may be performed using the method disclosed in JP-A-2007-257287, it may be determined that the deformation estimation process has failed when the area of a region (i.e., the number of pixels of a mask image that represents the region) that can be accurately subjected to registration is equal to or less than a given threshold value, and it may be determined that a scene change has occurred between the contiguous images for which the deformation estimation process has failed.

This makes it possible to reduce the number of images included in the input image sequence that is subjected to the process according to first embodiment (particularly the process that utilizes dynamic programming), and reduce the processing time. If the boundary between the partial image sequences is provided between the images for which the deformation estimation process has failed, it is unnecessary to use the deformation information about these images when performing the process. Specifically, since the process does not use the deformation information that is inaccurate to such an extent that it has been determined that the deformation estimation process has failed, it is possible to improve the accuracy (e.g., the coverage calculation accuracy) of the process that utilizes the deformation information.

Figure 11A:
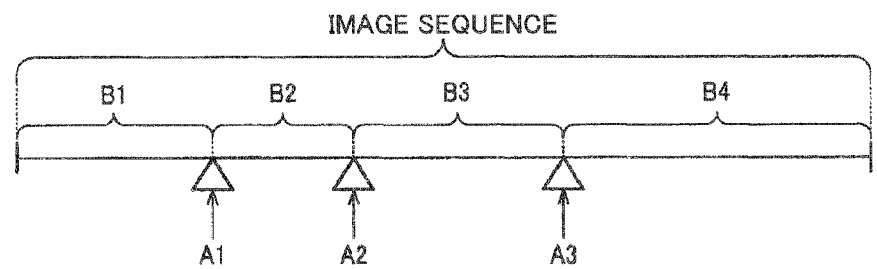
FIGS. 11A and 11B are views illustrating the relationship between a scene change and a partial image sequence.
Figure 11B:
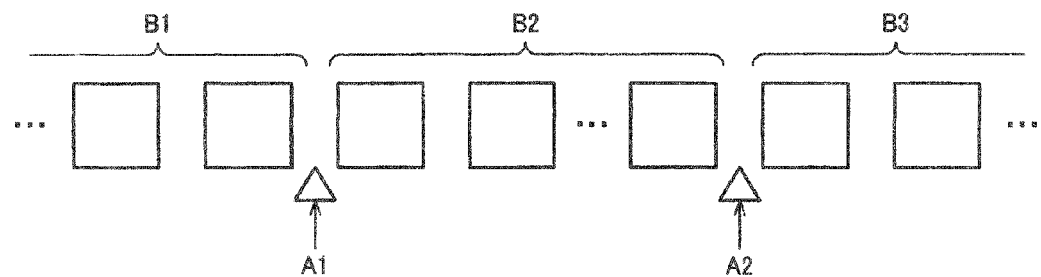

As illustrated in FIGS. 11A and 11B, when three scene changes A1 to A3 have been detected from the image sequence, four partial image sequences B1 to B4 may be set to be divided at the scene changes A1 to A3.

When a plurality of partial image sequences have been set based on a scene change, the plurality of partial image sequences need not necessarily be sequentially processed one by one. When the configuration of the processing section 100 is suitable for parallel processing (e.g., when a CPU that includes a plurality of cores is used as the processing section 100), or when the image processing device according to the first embodiment is implemented by a plurality of computers, and distributed processing is performed by each computer, the image summarization process may be performed on the plurality of partial image sequences in parallel. This makes it possible to reduce the time required for the image summarization process, for example.

According to the first embodiment, the image processing device includes the image sequence acquisition section 200 that acquires an input image sequence that includes first to Nth (N is an integer equal to or larger than 2) images as constituent images, and the processing section 100 that performs the image summarization process that deletes some of the first to Nth images included in the input image sequence acquired by the image sequence acquisition section 200 to generate a summary image sequence (see FIG. 1 or 21). The processing section 100 selects an s-th (s is an integer that satisfies $0 \leq s \leq N+1$) image included in the input image sequence to be the provisional summary image, selects a t-th (t is an integer that satisfies $0 \leq t \leq s-1$) image included in the input image sequence to be the provisional preceding summary image, and selects a u-th (u is an integer that satisfies $t < u < s$) image included in the input image sequence to be the determination target image. The processing section 100 calculates the deletion evaluation value of the determination target image based on the deformation information about the provisional summary image and the determination target image, and the deformation information about the provisional preceding summary image and the determination target image, calculates the summarization interval evaluation value $G(t, s)$ that is the evaluation value when the (t+1)-th to (s−1)-th images are deleted based on the deletion evaluation values of the (t+1)-th to (s−1)-th images, and performs the image summarization process based on the summarization interval evaluation value.

This makes it possible to implement the image summarization process based on the summarization interval evaluation value. The summarization interval evaluation value $G(t, s)$ is the evaluation value when the t-th image and the s-th image are allowed to remain in the summary image sequence, and all of the (t+1)-th to (s−1)-th images are deleted. Specifically, when an a-th image, a b-th image, and a c-th image are allowed to remain in the summary image sequence, the evaluation value of the summary image sequence can be calculated from the summarization interval evaluation value $G(a, b)$ and the summarization interval evaluation value $G(b, c)$. Note that the summarization interval evaluation value $G(0, a)$ and the summarization interval evaluation value $G(c, N+1)$ are also used when the zero-th image and the (N+1)-th image are provided as virtual images. Therefore, it is possible to calculate the evaluation value of an arbitrary summary image sequence generated from the input image sequence by calculating all of the summarization interval evaluation values between two arbitrary images among the first to Nth images, and find (search) the optimum summary image sequence from a plurality of candidates for the summary image sequence. The summarization interval evaluation value G may be calculated corresponding to all of the combinations of two images among the first to Nth images (or the zero-th to (N+1)-th images (including the virtual images)). Note that some of the summarization interval evaluation values G may not be calculated from the viewpoint of reducing the amount of calculations. Since the summarization interval evaluation value is calculated based on the deformation information about images, it is possible to control the degree by which an area that cannot be observed occurs due to deletion of an image.

The processing section 100 may calculate the total evaluation values $E(1)$ to $E(N)$ of the first to Nth images based on the summarization interval evaluation value, and perform the image summarization process based on the total evaluation values.

This makes it possible to implement the image summarization process based on the total evaluation values. The total evaluation value E(k) represents the optimum evaluation value among the evaluation values on the assumption that the zero-th image and the k-th image are allowed to remain in the summary image sequence. Note that the (k+1)-th to (N+1)-th images are not taken into consideration. When allowing the zero-th image and the k-th image to remain in the summary image sequence, each of the first to (k−1)-th images is either allowed to remain in the summary image sequence, or deleted. Therefore, the total evaluation value E(k) represents the optimum combination (or the combination that has been determined to be optimum) among $2^{k-1}$ combinations. Specifically, it is possible to determine the optimum combination as to whether or not to delete the first to (k−1)-th images on the assumption that the k-th image is allowed to remain in the summary image sequence, by calculating the total evaluation value E(k). This means that the optimum combination as to whether or not delete the first to Nth images can be determined by calculating the total evaluation value E(N+1) of the (N+1)-th image (virtual image). This process is a process that globally calculates the optimum summary image sequence. Note that the first embodiment may utilize dynamic programming in order to reduce the amount of calculations. In this case, the total evaluation value E is sequentially calculated from the image closest to the start point (zero-th image) instead of directly calculating the total evaluation value E(N+1), and the previous processing results (E(1) to E(k−1)) are used when calculating the total evaluation value E(k) of a given image. Therefore, the first embodiment implements the image summarization process by calculating the total evaluation values E(1) to E(N) of the first to Nth images.

The processing section 100 may calculate the total evaluation value of the zero-th image that is a virtual image to be E(0)=0, and calculate the total evaluation value of a v-th (v is an integer that satisfies 1≤v≤N+1) image by calculating E(v)= max(E(w)+G(w, v)) using the total evaluation value E(w) of a w-th (w is an integer that satisfies 0≤w≤v−1) image, and the summarization interval evaluation value G(w, v) when the (w+1)-th to (v−1)-th images are deleted.

This makes it possible to calculate the total evaluation value E using dynamic programming. In this case, the total evaluation value E(v) can be calculated by calculating "E+G" v times, and calculating the optimum value (i.e., the largest value in a narrow sense) without taking account of all of the combinations as to whether or not to delete the zero-th to v-th images. Specifically, it is possible to significantly reduce the amount of calculations as compared with the case of directly calculating the total evaluation value E(N+1) (although it is necessary to calculate the total evaluation values E(1) to E(N)).

The processing section 100 may select an x-th image that satisfies the following expression (1) to be the optimum preceding summary image that precedes the v-th image.

$$x = \mathrm{argmax}_w(E(w) + G(w, v)) \quad (1)$$

The processing section 100 may calculate the total evaluation value E(N+1) of the (N+1)-th image that is a virtual image, and set the (N+1)-th image to be the first processing target image during the summary image sequence determination process. The processing section 100 may allow the optimum preceding summary image to remain in the summary image sequence, update the processing target image with the optimum preceding summary image, and continue the summary image sequence determination process, when the optimum preceding summary image that precedes the processing target image is not the zero-th image. The processing section 100 may terminate the summary image sequence determination process when the optimum preceding summary image that precedes the processing target image is the zero-th image.

This makes it possible to select the optimum preceding summary image that precedes the v-th image when calculating the total evaluation value E(v), and perform the summary image sequence determination process using the optimum preceding summary image. When implementing dynamic programming, it suffices to determine the preceding node that immediately precedes the processing target node, and it is unnecessary to take account of the path from the start point to the preceding node when processing the processing target node, from the viewpoint of utilizing the previous processing results. However, the optimum path can be determined by determining the preceding node that immediately precedes each node, and sequentially tracing the preceding nodes from the end point. In the first embodiment, this process is applied to an image sequence. Specifically, the provisional preceding summary image that maximizes the provisional total evaluation value of the provisional summary image is determined to be the optimum preceding summary image. The summary image sequence determination process traces the optimum preceding summary images from the (N+1)-th image to the zero-th image.

The processing section 100 may calculate the coverage of the u-th image based on the deformation information about the s-th image and the u-th image, and the deformation information about the t-th image and the u-th image, the coverage of the u-th image being the ratio in which the u-th image is covered by the s-th image and the t-th image. The processing section 100 may calculate the deletion evaluation value based on the coverage, and calculate a value obtained by adding up the deletion evaluation values of the (t+1)-th to (s−1)-th images to be the summarization interval evaluation value G(t, s) when the (t+1)-th to (s−1)-th images are deleted.

This makes it possible to calculate the summarization interval evaluation value based on the coverage. For example, the coverage may be calculated using the coverage area (see FIGS. 2 and 3), or may be calculated using another method. In this case, since the coverage is used to calculate the summarization interval evaluation value, it is expected that the summary image sequence determined based on the summarization interval evaluation value has a high coverage (i.e., a summary image sequence for which occurrence of an area that cannot be observed is suppressed).

The processing section 100 may determine whether or not the u-th image can be deleted based on the deformation information about the s-th image and the u-th image, and the deformation information about the t-th image and the u-th image. The processing section 100 may set a first value to be the summarization interval evaluation value G(t, s) when the (t+1)-th to (s−1)-th images are deleted, when it has been determined that at least one constituent image among the (t+1)-th to (s−1)-th images cannot be deleted.

In this case, the processing section 100 may set the first value to negative infinity, or a value that is equal to or smaller than a given threshold value determined based on the total evaluation value.

This makes it possible to set a given value to be the evaluation value of the summary image sequence without taking account of the number of images that can be deleted, the coverage, and the like, when it has been determined that at least one constituent image among the (t+1)-th to (s−1)-th images cannot be deleted (i.e., when the images between the t-th image and the s-th image cannot be sufficiently covered by the t-th image and the s-th image). Specifically, a value that prevents a situation in which the t-th image is selected to be the optimum preceding summary image that precedes the s-th image is set to be the evaluation value of the summary image sequence. Since it is desirable that the total evaluation value be large, the provisional total evaluation value calculated using the summarization interval evaluation value that is the first value is necessarily smaller than the provisional total evaluation value calculated using the summarization interval evaluation value that is a value other than the first value (corresponding to the case where all of the (t+1)-th to (s−1)-th images can be deleted) when −∞ is used as the first value.

Note that the first value need not necessarily be −∞ as long as the relationship "(largest provisional total evaluation value when image cannot be deleted)<(smallest provisional total evaluation value when image can be deleted)" is satisfied. In this case, the first value is determined based on the total evaluation value since the provisional total evaluation value is determined by the total evaluation value of the provisional preceding summary image and the summarization interval evaluation value. For example, the first value may be a negative value of which the absolute value is large to such an extent that the order differs to a large extent from a value that is considered to be the total evaluation value. Alternatively, the first value may be a value that is smaller than the value "(minimum value that may be used as total evaluation value of provisional summary image)−(total evaluation value of provisional preceding summary image). In this case, the condition whereby the t-th image is not selected to be the optimum preceding summary image that precedes the s-th image, is also satisfied.

The processing section 100 may calculate the summarization interval evaluation value G(t, s) when the (t+1)-th to (s−1)-th images are deleted, based on the number of the (t+1)-th to (s−1)-th images, when it has been determined that all of the (t+1)-th to (s−1)-th images can be deleted.

This makes it possible to calculate the summarization interval evaluation value based on the number of images that can be deleted. Since the number of images included in the summary image sequence can be reduced as the number of images that can be deleted increases, the effects of the image summarization process can be improved. Note that whether or not an image can be deleted may be determined by comparing the coverage with a given threshold value (k1) (see above). Note that the configuration is not limited thereto. For example, whether or not an image can be deleted may be determined based on the results of the erosion processing that utilizes the structural element (see the second embodiment), or may be determined by combining two methods (see FIG. 20).

The processing section 100 may select the t-th image to be the provisional preceding summary image while updating t by −1 from t=s−1 to t=0, and perform a termination determination process based on the deformation information about the t-th image and the u-th image, and the deformation information about the s-th image and the u-th image. The processing section 100 may set the first value to be the summarization interval evaluation value G(x, s) when the constituent image between an x-th (x is an integer that satisfies 0≤x≤t) image and the s-th image is deleted, and terminate the process in which the s-th image is selected to be the provisional summary image.

This makes it possible to implement the termination determination process. It is considered that it is likely that images that are included in the image sequence and situated close to each other within the image sequence are similar images (see above). Specifically, when the degree of coverage of the (t+1)-th to (s−1)-th images by the t-th image and the s-th image is very low, it is considered that the degree of coverage of the t-th to (s−1)-th images by the (t−1)-th image and the s-th image is also low even if the provisional preceding summary image is updated. In this case, it is unlikely that a problem will occur when the process in which the zero-th to (t−1)-th images are selected to be the provisional preceding summary image is skipped, and the amount of calculations can be reduced by skipping the process. In this case, the first value may be set to be the summarization interval evaluation value when the zero-th to (t−1)-th images are selected to be the provisional preceding summary image.

The processing section 100 may select (s−α)-th (α is a positive integer) to (s−1)-th images among the zero-th to (s−1)-th images to be the provisional preceding summary image.

This makes it possible to narrow the provisional preceding summary image setting range (i.e., a range within which the optimum preceding summary image is searched), and reduce the amount of calculations. The input image sequence used in connection with the first embodiment has a tendency in which it is unlikely that the images between the provisional summary image and the provisional preceding summary image can be covered when the number of images between the provisional summary image and the provisional preceding summary image is too large. Specifically, when the provisional preceding summary image is set at a position significantly away from the provisional summary image, it is unlikely that the provisional preceding summary image is determined to be the optimum preceding summary image, and it may not be useful to perform the process on such a provisional preceding summary image. Therefore, the provisional preceding summary image setting range may be limited.

The processing section 100 may detect a scene change from the input image sequence, set constituent images among the plurality of constituent images included in the input image sequence that follow an i-th (i is an integer) scene change and precede an (i+1)-th scene change, to be a partial image sequence, when the i-th scene change and the (i+1)-th scene change that follows the i-th scene change have been detected from the input image sequence, and perform the image summarization process on the partial image sequence.

This makes it possible to divide the input image sequence into a plurality of partial image sequences, and perform the process on each partial image sequence. The processing time of dynamic programming is proportional to the second power of the processing interval length. It is possible to reduce the processing time by performing the process on each partial image sequence. The processing time may be further reduced by performing the process on a plurality of partial image sequences in parallel.

Note that part or most of the process performed by the image processing device and the like according to the first embodiment may be implemented by a program. In this case, the image processing device and the like according to the first embodiment are implemented by causing a processor (e.g., CPU) to execute a program. Specifically, a program stored in a non-transitory information storage device is read, and executed by a processor (e.g., CPU). The information storage device (computer-readable device) stores a program, data, and the like. The function of the information storage device may be implemented by an optical disk (e.g., DVD or CD), a hard disk drive (HDD), a memory (e.g., memory card or ROM), or the like. The processor (e.g., CPU) performs various processes according to the first embodiment based on the program (data) stored in the information storage device. Specifically, a program that causes a computer (i.e., a device that includes an operation section, a processing section, a storage section, and an output section) to function as each section according to the first embodiment (i.e., a program that causes a computer to execute the process implemented by each section) is stored in the information storage device.

The image processing device and the like according to the first embodiment may include a processor and a memory. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The memory stores computer-readable instructions. Each section of the endoscope apparatus and the like according to the first embodiment is implemented by causing the processor to execute the instructions. The memory may be a semiconductor memory (e.g., SRAM or DRAM), a register, a hard disk, or the like. The instructions may be instructions included in an instruction set that forms a program, or may be instructions that cause a hardware circuit of the processor to operate.

3. Second Embodiment

A method that determines the probability that the attention area is missed based on the erosion process that utilizes the structural element is described below.

3.1 System Configuration Example

Figure 13:
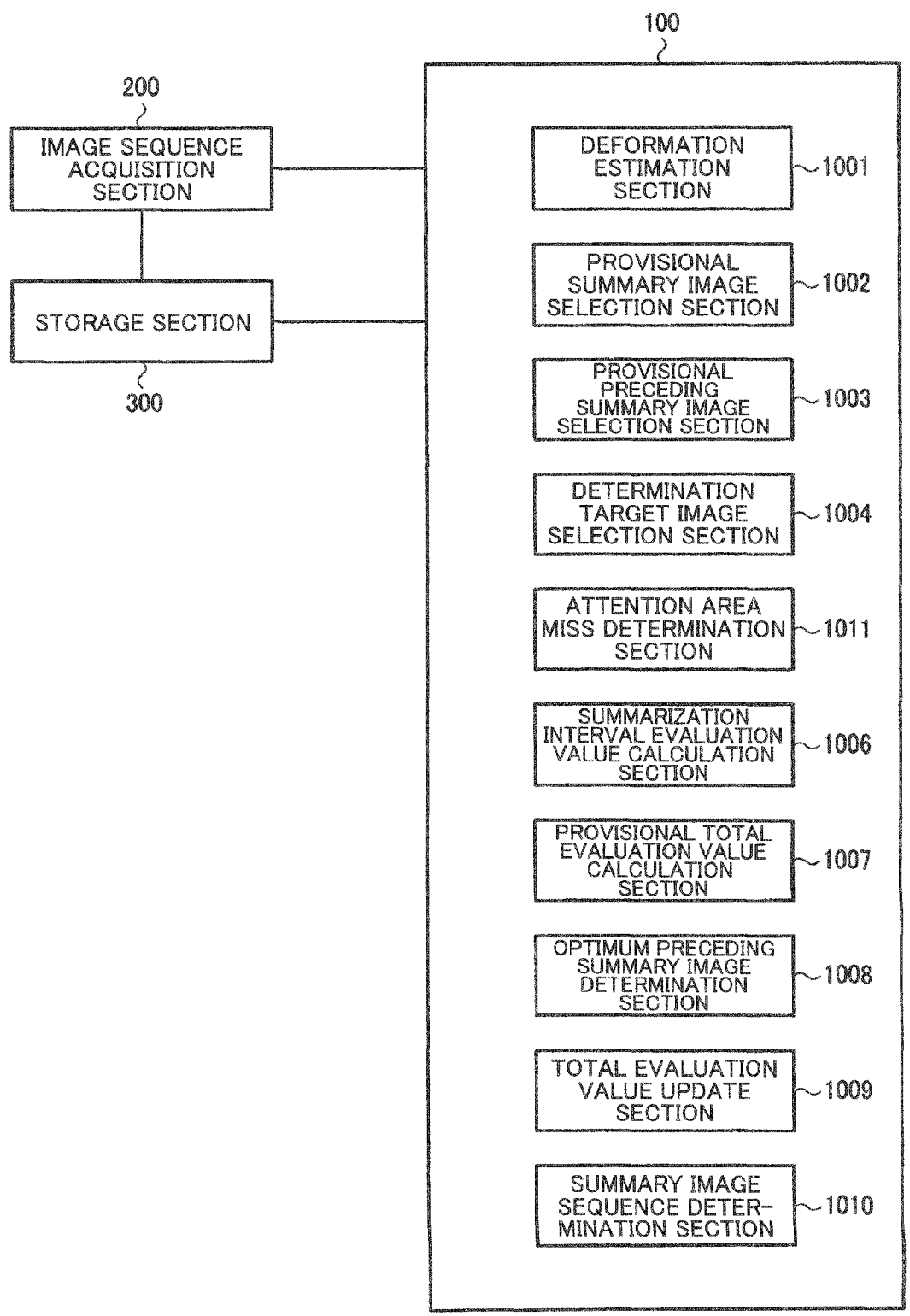
FIG. 13 illustrates a configuration example of an image processing device (second embodiment).

FIG. 13 illustrates a configuration example of the image processing device according to the second embodiment. As illustrated in FIG. 13, the image processing device according to the second embodiment differs from the image processing device according to the first embodiment (see FIG. 1) in that the coverage calculation section 1005 is omitted, and an attention area miss determination section 1011 is additionally provided. The remaining sections are the same as described above in connection with the first embodiment, except for the way in which the summarization interval evaluation value calculation section 1006 calculates the summarization interval evaluation value G, and detailed description of each section is appropriately omitted.

When the provisional summary image, the provisional preceding summary image, and the determination target image have been selected, the attention area miss determination section 1011 performs a determination process that determines the probability that the attention area captured within the determination target image is not captured within the provisional summary image and the provisional preceding summary image (i.e., the attention area is missed) when the determination target image is deleted.

3.2 Attention Area Miss Probability Determination Process and Summarization Interval Evaluation Value Calculation Processes A specific flow of the process is described below. The attention area miss determination section 1011 generates the structural element based on the attention area (e.g., a lesion that should not be missed when using a capsule endoscope). The attention area miss determination section 1011 sets an area having a size and a shape that should not be missed to be the structural element taking account of a typical size and the like of the attention area. For example, when the attention area is a lesion, and a lesion that is larger than a circle having a diameter of 30 pixels within the image is severe, and should not be missed, a circle having a diameter of 30 pixels is set to be the structural element.

When the provisional summary image, the provisional preceding summary image, and the determination target image have been selected, first deformation information about the provisional summary image and the determination target image, and second deformation information about the provisional preceding summary image and the determination target image, are acquired using the results of the deformation estimation process performed by the deformation estimation section 1001. The provisional summary image and the provisional preceding summary image are projected onto the determination target image by utilizing the acquired deformation information to calculate the coverage area in the same manner as in the first embodiment.

When the coverage area has been calculated, the attention area miss determination section 1011 determines the probability that the attention area is missed. Specifically, the attention area miss determination section 1011 performs the erosion process that utilizes the structural element on the non-coverage area (i.e., an area other than the coverage area) of the determination target image to determine whether or not a residual area is present (see FIG. 14).

A specific example of the erosion process is described below with reference to FIGS. 15A to 15E. As illustrated in FIG. 15A, the non-coverage area is necessarily a closed area, and the boundary of the non-coverage area can be set. For example, an outer boundary BO1 and an inner boundary BO2 are set in FIG. 15A.

The erosion process that utilizes the structural element removes the overlapping area of the non-coverage area and the structural element when a reference point of the structural element is set at the boundary of the non-coverage area. For example, when a circular area is set to be the structural element, and the reference point of the structural element is the center of the circle, the erosion process draws a circle so that the center of the circle is situated at the boundary of the non-coverage area, and excludes the overlapping area of the circle and the non-coverage area from the non-coverage area. Specifically, a circle is drawn around a point situated at the outer boundary BO1 of the non-coverage area (see FIG. 15A), and the overlapping area of the circle and the non-coverage area (i.e., the semicircular area indicated by the diagonal lines in FIG. 15A) is excluded from the non-coverage area.

Since the outer boundary BO1 is processed discretely, and includes a plurality of points, the above process may be performed on each point among the plurality of points. For example, a circle may be sequentially drawn around each point situated at the outer boundary BO1 in a given direction (see FIG. 15A), and the overlapping area of each circle and the non-coverage area may be excluded from the non-coverage area.

When part of the boundary of the non-coverage area coincides with the boundary of the determination target image, for example, the non-coverage area may have only a single boundary. In such a case, the above process may be performed on the single boundary. When the non-coverage area has the outer boundary BO1 and the inner boundary BO2 (see FIG. 15A), the above process is performed on the outer boundary BO1 and the inner boundary BO2. Specifically, a circle is drawn around each point situated at the inner boundary BO2 (see FIG. 15B), and the overlapping area of each circle and the non-coverage area is excluded from the non-coverage area.

The non-coverage area is reduced as a result of the erosion process. For example, the left part of the non-coverage area illustrated in FIG. 15A is completely deleted (i.e., no residual area is present) by the erosion process performed on the outer boundary BO1 (see FIG. 15A) and the erosion process performed on the inner boundary BO2 (see FIG. 15B). On the other hand, a residual area RE that is not excluded by the erosion process performed on the outer boundary BO1 and the erosion process performed on the inner boundary BO2 occurs in the lower right part of the non-coverage area (see FIG. 15C). Specifically, only the residual area RE remains as a result of performing the erosion process that utilizes the structural element over the entire non-coverage area (see FIG. 15D).

The meaning of the erosion process when using a circle having a radius r as the structural element is discussed below. The non-coverage area (i.e., closed area) is considered to be an area that is surrounded by a boundary (different boundaries (e.g., BO1 and BO2) or a single boundary). When the erosion process is performed on the boundary, a point among the points included in the non-coverage area that is situated at a distance equal to or shorter than r from each point situated at the boundary is determined to be the deletion target. Specifically, the distance from the point included in the residual area (that is excluded from the deletion target) to an arbitrary point situated at the boundary is longer than r. Therefore, a circle having a radius r that is drawn around an arbitrary point within the residual area does not intersect each boundary. This means that the entirety of the attention area represented by a circle having a radius r that is drawn around a point within the residual area is included within the non-coverage area. Note that the above basic idea is also applied even when the structural element has a shape (e.g., quadrangle) other than a circle.

Figure 15C:
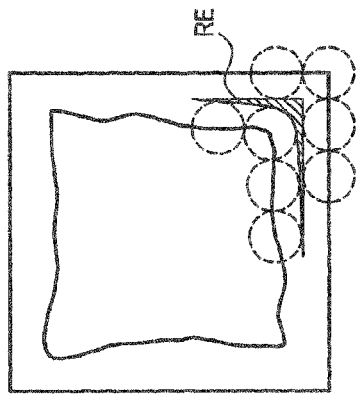
FIGS. 15A to 15E are views illustrating the details of a erosion process that utilizes a structural element, and is performed on a non-coverage area.
Figure 15B:
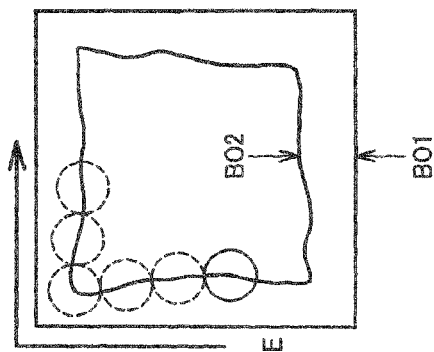
Figure 15E:
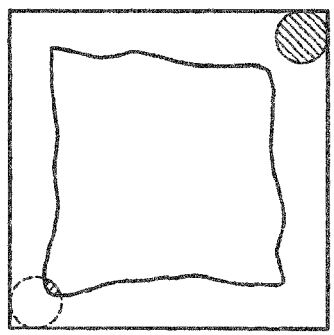
Figure 15A:
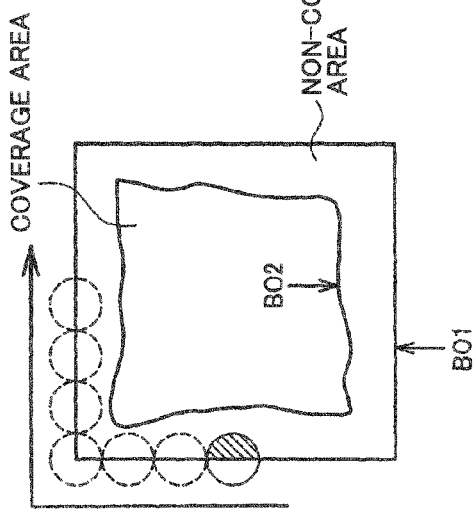
Figure 15D:

Specifically, when the residual area is present, an area that corresponds to the structural element is included within the non-coverage area (see the lower right part in FIG. 15E). When the attention area (e.g., lesion) is situated at such a position, and the determination target image is deleted, it is likely that the attention area cannot be observed even if the reference image is allowed to remain. When the residual area is not present, at least part of the attention area is included within the coverage area (see the upper left part in FIG. 15E). In this case, at least part of the attention area remains in the reference image even if the determination target image is deleted. Accordingly, the attention area miss determination section 1011 performs the erosion process that utilizes the structural element on the non-coverage area, and determines whether or not the determination target image can be deleted based on whether or not the residual area is present.

The summarization interval evaluation value calculation section 1006 according to the second embodiment calculates the summarization interval evaluation value based on the results of the above deletion determination process. Specifically, when it has been determined that all of the images between the provisional summary image and the provisional preceding summary image can be deleted, the summarization interval evaluation value calculation section 1006 sets the number of images that can be deleted (i.e., the number of images included in the summarization interval) to be the summarization interval evaluation value. When it has been determined that at least one of the images between the provisional summary image and the provisional preceding summary image cannot be deleted, the summarization interval evaluation value calculation section 1006 sets a sufficiently small value (e.g., $-\infty$) to be the summarization interval evaluation value.

The process performed after the summarization interval evaluation value has been calculated is the same as described above in connection with the first embodiment.

3.3 Details of Process

Figure 16:
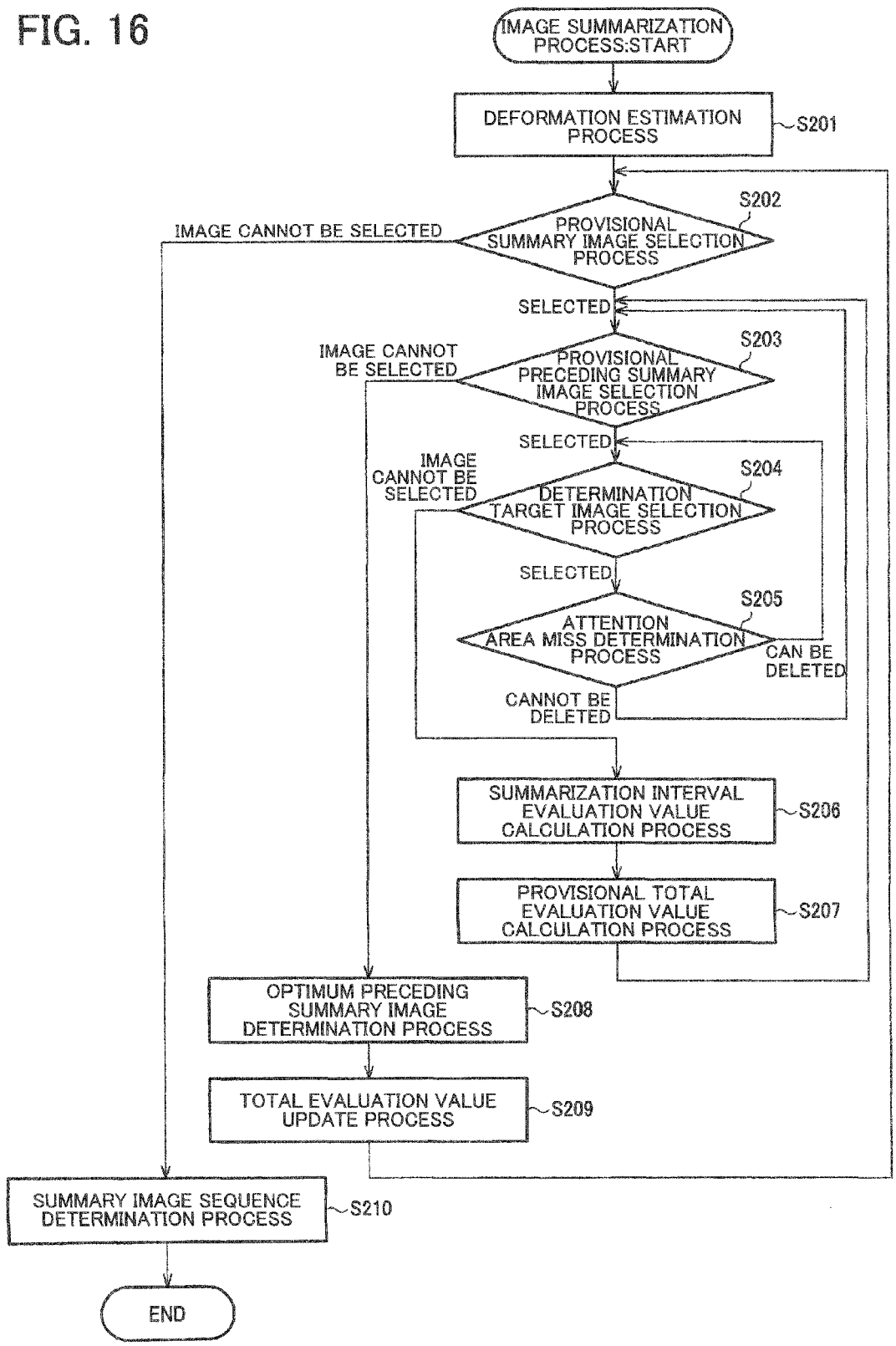
FIG. 16 is a flowchart illustrating an image summarization process (second embodiment).

The flow of the image summarization process according to the second embodiment is described below with reference to FIG. 16 (flowchart). Note that the steps S201 to S204 are respectively the same as the steps S101 to S104 illustrated in FIG. 4. When the determination target image has been selected in the step S204, the probability that the attention area is missed is determined as described above with reference to FIGS. 15A to 15E. When it has been determined that the determination target image can be deleted (i.e., when the residual area is not present), the step S204 is performed. When it has been determined that the determination target image cannot be deleted (i.e., when the residual area is present), a sufficiently small value is set to be the summarization interval evaluation value, and the provisional preceding summary image is updated in the step S203.

When an image cannot be selected in the step S204 (i.e., when all of the determination target images can be deleted), the number of images between the provisional summary image and the provisional preceding summary image is calculated to be the summarization interval evaluation value (S206). The subsequent steps S207 to S210 are respectively the same as the steps S107 to S210 illustrated in FIG. 4, and detailed description thereof is omitted.

3.4 Modifications

Figure 17A:
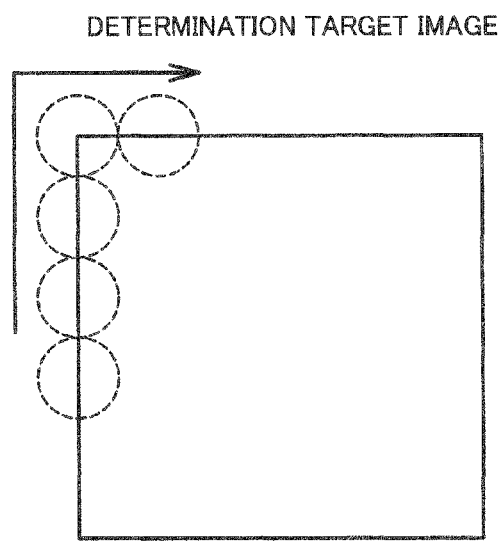
FIGS. 17A and 17B are views illustrating a erosion process that utilizes a structural element, and is performed on a determination target image.
Figure 17B:
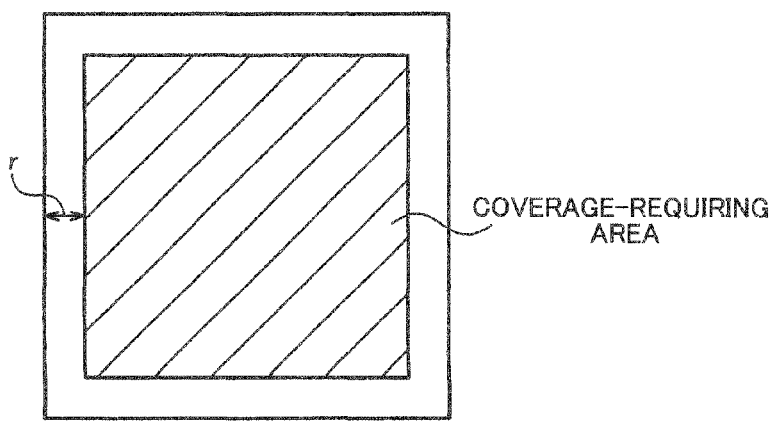

The target of the erosion process that utilizes the structural element is not limited to the non-coverage area. For example, the erosion process that utilizes the structural element may be performed on the determination target image (see FIG. 17A). In this case, a coverage-requiring area that must be covered by the reference image remains (see FIG. 17B) by setting the structural element so that the entirety of the attention area is not included within the area that is removed by the erosion process (e.g., setting an element having a size twice that of the attention area as the structural element). Specifically, whether or not the determination target image can be deleted may be determined based on whether or not the entirety of the coverage-requiring area is covered by at least one of the provisional summary image and the provisional preceding summary image. More specifically, the provisional summary image and the provisional preceding summary image may be deformed using the deformation information to calculate the coverage area, and the inclusion determination process may be performed using the coverage area and the coverage-requiring area (see FIG. 18). The determination target image can be deleted when the coverage-requiring area is included within the coverage area, and cannot be deleted when the entirety of the coverage-requiring area is not included within the coverage area.

Figure 19A:
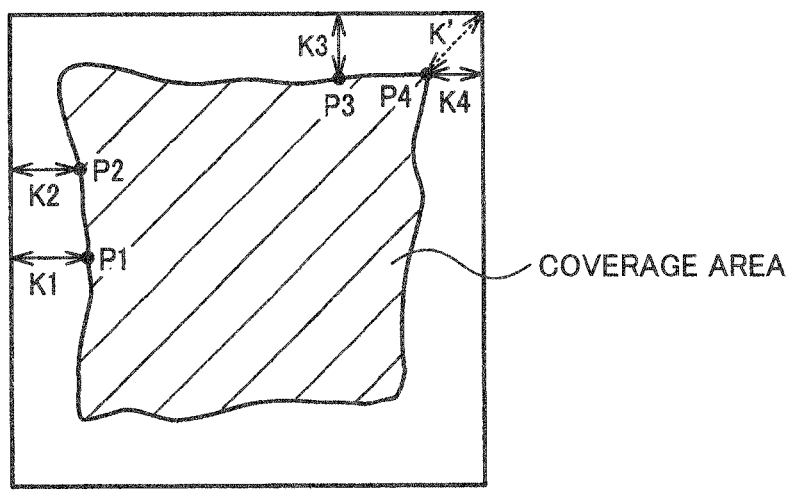
FIGS. 19A and 19B are views illustrating another process that utilizes a structural element.
Figure 19B:
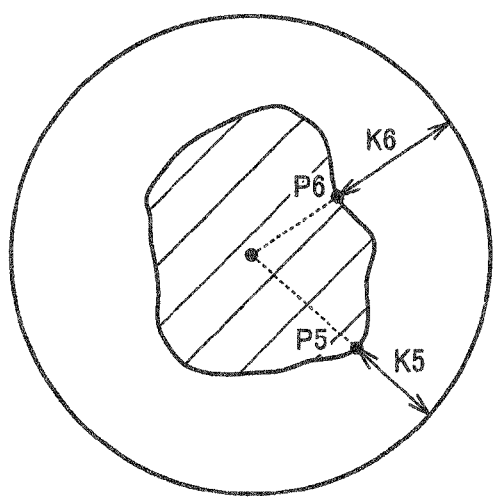

The deletion determination process that utilizes the structural element is not limited to the deletion determination process that utilizes the erosion process. It suffices that the deletion determination process that utilizes the structural element determine whether or not the structural element is included in the non-coverage area. For example, the deletion determination process that utilizes the structural element may be implemented using a simple method that calculates a value that corresponds to the maximum size (diameter) of the non-coverage area based on the distance (e.g., k1 to k6) from the point (e.g., p1 to p6) at the boundary of the coverage area to the boundary of the determination target image, or the distance from the point at the boundary of the determination target image to the boundary of the coverage area, and compares the calculated value with the minimum size of the structural element (e.g., a structural element having the size as that of the attention area) (see FIGS. 19A and 19B). Note that FIG. 19A illustrates an example in which the determination target image has a square shape, and FIG. 19B illustrates an example in which the determination target image has a circular shape.

The coverage calculation process described above in connection with the first embodiment may be combined with the attention area miss probability determination process described above in connection with the second embodiment. For example, both the coverage calculation process and the attention area miss probability determination process may be performed in the step S105 illustrated in FIG. 4 or the step S205 illustrated in FIG. 16, and the branch process illustrated in FIG. 20 may be performed.

Specifically, the determination target image is updated in the step S104 when it has been determined that the determination target image can be deleted based on the coverage and the attention area miss probability, and the summarization interval evaluation value G is calculated in the step S106 using the coverage and the number of images that can be deleted when it has been determined that all of the images can be deleted. When it has been determined that the determination target image cannot be deleted based on at least one of the coverage and the attention area miss probability, a sufficiently small value is set to be the summarization interval evaluation value. When it has been determined to terminate the process based on the coverage, the process may be terminated in the same manner as in the first embodiment.

This makes it possible to improve the accuracy when determining whether or not the determination target image can be deleted, and calculate a more appropriate summary image sequence.

The first and second embodiments to which the invention is applied, and the modifications thereof, have been described above. Note that the invention is not limited to the first and second embodiments and the modifications thereof. The elements may be modified in various ways within the scope of the invention when implementing the invention. A plurality of elements of each of the first and second embodiments and the modifications thereof may be appropriately combined to implement various configurations. For example, an arbitrary element may be omitted from the elements described above in connection with the first and second embodiments and the modifications thereof. Some of the elements described above in connection with different embodiments or modifications thereof may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An image processing device comprising:
   an image sequence acquisition section that acquires an input image sequence that includes first to N-th (N is an integer equal to or larger than 2) images as constituent images; and
   a processing section that performs an image summarization process that deletes some of the first to Nth images included in the input image sequence acquired by the image sequence acquisition section to generate a summary image sequence,
   the processing section selecting an s-th (s is an integer that satisfies $0 \le s \le N+1$) image included in the input image sequence to be a provisional summary image, selecting a t-th (t is an integer that satisfies $0 \le t \le s-1$) image included in the input image sequence to be a provisional preceding summary image, selecting a u-th (u is an integer that satisfies $t<u<s$) image included in the input image sequence to be a determination target image, calculating a deletion evaluation value of the determination target image based on deformation information about the provisional summary image and the determination target image, and the deformation information about the provisional preceding summary image and the determination target image, calculating a summarization interval evaluation value $G(t, s)$ that is an evaluation value when $(t+1)$-th to $(s-1)$-th images are deleted, based on the deletion evaluation values of the $(t+1)$-th to $(s-1)$-th images, and performing the image summarization process based on the summarization interval evaluation value.

2. The image processing device as defined in claim 1,
the processing section calculating total evaluation values $E(1)$ to $E(N)$ of the first to Nth images based on the summarization interval evaluation value, and performing the image summarization process based on the total evaluation values.

3. The image processing device as defined in claim 2,
the processing section calculating the total evaluation value of a zero-th image that is a virtual image to be $E(0)=0$, and calculating the total evaluation value of a v-th (v is an integer that satisfies $1 \le v \le N+1$) image by calculating $E(v)=\max(E(w)+G(w, v))$ using the total evaluation value $E(w)$ of a w-th (w is an integer that satisfies $0 \le w \le v-1$) image, and the summarization interval evaluation value $G(w, v)$ when $(w+1)$-th to $(v-1)$-th images are deleted.

4. The image processing device as defined in claim 3,
the processing section selecting an x-th image that satisfies an expression shown below to be an optimum preceding summary image the precedes the v-th image, $$x = \underset{w}{\operatorname{argmax}}(E(w) + G(w, v)).$$

5. The image processing device as defined in claim 4,
the processing section calculating the total evaluation value $E(N+1)$ of an $(N+1)$-th image that is the virtual image, setting the $(N+1)$-th image to be a first processing target image during a summary image sequence determination process, allowing the optimum preceding summary image to remain in the summary image sequence, updating the processing target image with the optimum preceding summary image, and continuing the summary image sequence determination process, when the optimum preceding summary image that precedes the processing target image is not the zero-th image, and terminating the summary image sequence determination process when the optimum preceding summary image that precedes the processing target image is the zero-th image.

6. The image processing device as defined in claim 1,
the processing section calculating a coverage of the u-th image based on the deformation information about the s-th image and the u-th image, and the deformation information about the t-th image and the u-th image, the coverage of the u-th image being a ratio in which the u-th image is covered by the s-th image and the t-th image, calculating the deletion evaluation value based on the coverage, and calculating a value obtained by adding up the deletion evaluation values of the (t+1)-th to (s−1)-th images to be the summarization interval evaluation value G(t, s) when the (t+1)-th to (s−1)-th images are deleted.

7. The image processing device as defined in claim 1,
the processing section determining whether or not the u-th image can be deleted based on the deformation information about the s-th image and the u-th image, and the deformation information about the t-th image and the u-th image, and setting a first value to be the summarization interval evaluation value G(t, s) when the (t+1)-th to (s−1)-th images are deleted, when it has been determined that at least one constituent image among the (t+1)-th to (s−1)-th images cannot be deleted.

8. The image processing device as defined in claim 7,
the processing section calculating the summarization interval evaluation value G(t, s) when the (t+1)-th to (s−1)-th images are deleted, based on a number of the (t+1)-th to (s−1)-th images, when it has been determined that all of the (t+1)-th to (s−1)-th images can be deleted.

9. The image processing device as defined in claim 1,
the processing section selecting the t-th image to be the provisional preceding summary image while updating t by −1 from t=s−1 to t=0, performing a termination determination process based on the deformation information about the t-th image and the u-th image, and the deformation information about the s-th image and the u-th image, setting a first value to be the summarization interval evaluation value G(x, s) when the constituent image between an x-th (x is an integer that satisfies 0≤x≤t) image and the s-th image is deleted, with respect to t for which it has been determined by the termination determination process to terminate a process, and terminating a process in which the s-th image is selected to be the provisional summary image.

10. The image processing device as defined in claim 7,
the processing section setting the first value to negative infinity, or a value that is equal to or smaller than a given threshold value determined based on the total evaluation value.

11. The image processing device as defined in claim 1,
the processing section selecting (s−α)-th (α is a positive integer) to (s−1)-th images among zero-th to (s−1)-th images to be the provisional preceding summary image.

12. The image processing device as defined in claim 1,
the processing section detecting a scene change from the input image sequence, setting constituent images among the plurality of constituent images included in the input image sequence that follow an i-th (i is an integer) scene change and precede an (i+1)-th scene change, to be a partial image sequence, when the i-th scene change and the (i+1)-th scene change that follows the i-th scene change have been detected from the input image sequence, and performing the image summarization process on the partial image sequence.

13. An image processing method comprising:
acquiring an input image sequence that includes first to Nth (N is an integer equal to or larger than 2) images as constituent images;
selecting an s-th (s is an integer that satisfies 0≤s≤N+1) image included in the input image sequence to be a provisional summary image;
selecting a t-th (t is an integer that satisfies 0≤t≤s−1) image included in the input image sequence to be a provisional preceding summary image;
selecting a u-th (u is an integer that satisfies t<u<s) image included in the input image sequence to be a determination target image;
calculating a deletion evaluation value of the determination target image based on deformation information about the provisional summary image and the determination target image, and the deformation information about the provisional preceding summary image and the determination target image;
calculating a summarization interval evaluation value G(t, s) that is an evaluation value when (t+1)-th to (s−1)-th images are deleted, based on the deletion evaluation values of the (t+1)-th to (s−1)-th images; and
performing an image summarization process based on the summarization interval evaluation value, the image summarization process deleting some of the first to Nth images included in the input image sequence to generate a summary image sequence.

14. An information storage device storing a program that causes a computer to function as:
an image sequence acquisition section that acquires an input image sequence that includes first to Nth (N is an integer equal to or larger than 2) images as constituent images; and
a processing section that performs an image summarization process that deletes some of the first to Nth images included in the input image sequence acquired by the image sequence acquisition section to generate a summary image sequence,
the processing section selecting an s-th (s is an integer that satisfies 0≤s≤N+1) image included in the input image sequence to be a provisional summary image, selecting a t-th (t is an integer that satisfies 0≤t≤s−1) image included in the input image sequence to be a provisional preceding summary image, selecting a u-th (u is an integer that satisfies t<u<s) image included in the input image sequence to be a determination target image, calculating a deletion evaluation value of the determination target image based on deformation information about the provisional summary image and the determination target image, and the deformation information about the provisional preceding summary image and the determination target image, calculating a summarization interval evaluation value G(t, s) that is an evaluation value when (t+1)-th to (s−1)-th images are deleted based on the deletion evaluation values of the (t+1)-th to (s−1)-th images, and performing the image summarization process based on the summarization interval evaluation value.

\* \* \* \* \*